United States Patent

Häbich et al.

[11] Patent Number: 4,616,084
[45] Date of Patent: Oct. 7, 1986

[54] PROCESS FOR THE PREPARATION OF 7-ACYLAMINO-3-HYDROXY-CEPHEM-4-CARBOXYLIC ACIDS AND 7-ACYLAMINO-3-HYDROXY-1-DETHIA-1-OXACEPHEM-4-CARBOXYLIC ACIDS

[75] Inventors: Dieter Häbich; Wolfgang Hartwig, both of Wuppertal, Fed. Rep. of Germany

[73] Assignee: Bayer Aktiengesellschaft, Leverkusen, Fed. Rep. of Germany

[21] Appl. No.: 636,470

[22] Filed: Jul. 31, 1984

[30] Foreign Application Priority Data

Aug. 9, 1983 [DE] Fed. Rep. of Germany ....... 3328707
May 23, 1984 [DE] Fed. Rep. of Germany ....... 3419135

[51] Int. Cl.$^4$ ................. C07D 501/02; A61K 31/545
[52] U.S. Cl. ................... 540/215; 540/222; 540/301; 540/360; 540/203
[58] Field of Search ............................ 544/16, 22, 90

[56] References Cited

U.S. PATENT DOCUMENTS 4,174,316 11/1979 Christensen et al. ............ 260/239 A
4,346,218 8/1982 Tsujii et al. ............................ 544/16
4,550,162 10/1985 Woodward et al. ................... 544/25

FOREIGN PATENT DOCUMENTS 0019401 11/1980 European Pat. Off.
0081824 6/1983 European Pat. Off.

OTHER PUBLICATIONS

Habich et al., Tetrahedron, vol. 40, No. 19, pp. 3667–3676 (1984).
Ghosez et al., Tetrahedron, vol. 39, No. 15, 2493–2502 (1983).

*Primary Examiner*—Nicholas S. Pizzo
*Attorney, Agent, or Firm*—Sprung Horn Kramer & Woods

[57] ABSTRACT

A process for the preparation of a 7-acylamino-3-hydroxy-2-cephem-4-carboxylic acid, 7-acylamino-3-hydroxy-1-dethia-1-oxa-3-cephem-4-carboxylic acid or derivative thereof of the general formula

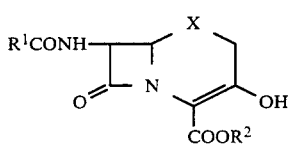

in which
R$^1$ is hydrogen or optionally substituted alkyl, alkenyl, alkinyl, aralkyl, aryl, heteroaryl, heteroaralkyl, aryloxyalkyl, heteroaryloxyalkyl, alkoxyalkyl, arylthioalkyl, heteroarylthioalkyl, alkylthioalkyl, alkoxy, aryloxy, alkylthio or arylthio, R$^2$ is hydrogen, a carboxy-protective group or a pharmaceutically useful ester radical, and
X is sulphur or oxygen,
which comprises:
(a) reacting a compound of the formula

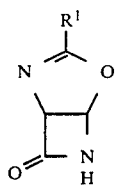

with
(i) a compound of the formula

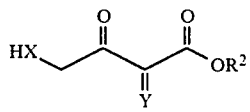

in which R$^2$ and X have the abovementioned meaning and Y represents diazo (N$_2$) or hydrogen (H$_2$) in an inert solvent in the presence of a Lewis acid or proton acid catalyst, or
(ii) a compound of the formula

HX—CH$_2$—C≡C—COOR$^2$ to form an intemediate compound having a triple bond, and hydrating the triple bond, the compounds thus obtained, for Y being hydrogen (H$_2$)—(in case of Y=diazo (N$_2$) directly the compounds of general formula (2) are obtained) thereby to produce a compound of the formula

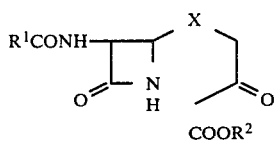

(b) reacting such compound with an azide in a solvent in the presence of a base to give a compound of the formula

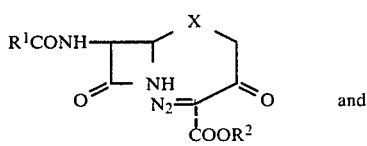

and (c) converting said compound to the desired product by
(i) irradiation in an inert solvent, or
(ii) warming in the presence of a catalyst.

The end products are, or can be converted to, known β-lactam antibiotics.

7 Claims, No Drawings

PROCESS FOR THE PREPARATION OF 7-ACYLAMINO-3-HYDROXY-CEPHEM-4-CARBOXYLIC ACIDS AND 7-ACYLAMINO-3-HYDROXY-1-DETHIA-1-OXACEPHEM-4-CARBOXYLIC ACIDS

The invention provides a process for the preparation of 7-acylamino-3-hydroxy-cephem-4-carboxylic acids and 7-acylamino-3-hydroxy-cephem-1-dethia-1-oxacephem-4-carboxylic acids.

The process according to the invention for the preparation of 7-acylamino-3-hydroxy-3-cephem-4-carboxylic acids and 7-acylamino-3-hydroxy-1-dethia-1-oxa-3-cephem-4-carboxylic acids and their derivatives of the general formula (1)

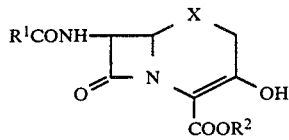

in which
$R^1$ represents hydrogen or optionally substituted alkyl, alkenyl, alkinyl, aralkyl, aryl, heteroaryl, heteroaralkyl, aryloxyalkyl, heteroaryloxyalkyl, alkoxyalkyl, arylthioalkyl, heteroarylthioalkyl, alkylthioalkyl, alkoxy, aryloxy, alkylthio or arylthio,
$R^2$ denotes hydrogen, a carboxy-protective group or a pharmaceutically useful ester radical and
X represents sulphur or oxygen,
is characterized in that compounds of the general formula (4)

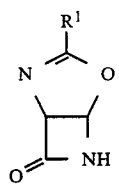

in which
$R^1$ has the abovementioned meaning,
(a) are reacted with a compound of the general formula (5)

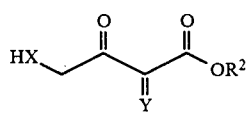

in which
$R^2$ and X have the abovementioned meaning and Y represents diazo ($N_2$) or hydrogen ($H_2$), in an inert solvent, such as, for example, methylene chloride or tetrahydrofuran, in the presence of a Lewis acid or proton acid catalyst, or
(b) are reacted with a compound of the general formula (6)

$$HX—CH_2—C\equiv C—COOR^2 \qquad (6)$$

in which
$R^2$ and X have the abovementioned meaning, as described under (a), the triple bond of the intermediate compound thereby formed is hydrated, the compounds thus obtained, for Y being hydrogen ($H_2$)—(in case of Y=diazo ($N_2$) directly the compounds of general formula (2) are obtained), of the general formula (3)

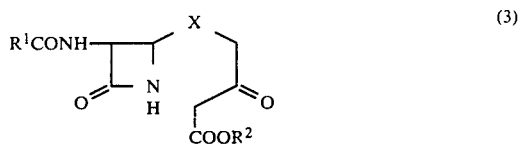

in which
$R^1$, $R^2$ and X have the abovementioned meaning, are reacted with an azide, such as, for example, 4-carboxybenzenesulphonyl azide, in a solvent, such as, for example, acetonitrile, in the presence of a base to give a compound of the general formula (2), and the compounds thus obtained, of the general formula (2)

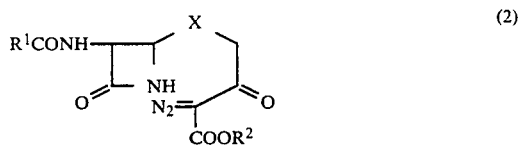

in which
$R^1$, $R^2$ and X have the abovementioned meaning, are converted to compounds of the general formula (1) in an inert solvent, such as, for example, benzene, by irradiation or by warming in the presence of a catalyst, such as, for example, rhodium-II acetate.

The compounds of the general formula (4) can be obtained by a process in which
(a) N-substituted oxazolinoazetidinones of the general formula (7)

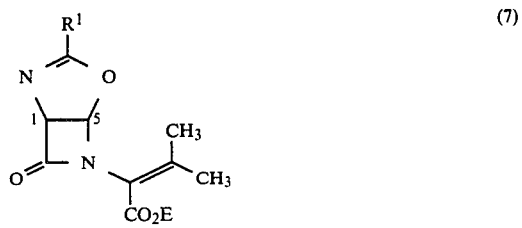

in which
$R^1$ has the abovementioned meaning and
$CO_2E$ represents an acid function $CO_2H$ or any desired ester function,
wherein
E represents the acid-protective groups usually employed in β-lactam chemistry, preferably a $C_1$–$C_4$-alkyl radical,
are reacted with an oxidizing agent under solvolytic conditions in a suitable solvent or solvent mixture, if appropriate in the presence of acid-binding agents or with subsequent use of reducing agents, or
(b) oxamides of the general formula (8)

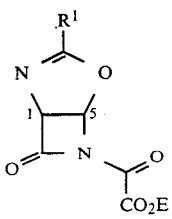

(8)

R[1] and CO$_2$E have the abovementioned meaning, are reacted under solvolytic conditions in a suitable solvent or solvent mixture, if appropriate in the presence of acids or bases.

The compounds of the general formula (7) in which R[1] and CO$_2$E have the meaning given can be obtained by processes analogous to known processes, by subjecting the olefinic bond of compounds of the general formula (9)

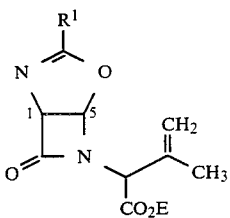

(9)

in which
R[1] and CO$_2$E have the abovementioned meaning, to isomerization in a suitable solvent in the presence of a base, such as is described, for example, by Y. Maki et al., J. C. S. Perkin I (1981) 2087, Y. Hamashima et al., Tetrahedron Lett. (1979) 2595, S. Uyeo et al., J. Am. Chem. Soc. 101, 4403 (1979) and in Belgian Patent Specification No. 862,793.

The oxazolino-oxamides of the general formula (8) can likewise be obtained by processes analogous to known processes, by subjecting the olefinic bond of azetidinones of the general formula (7), in which R[1] and CO$_2$E have the meaning given, to oxidative splitting, as is described analogously, for example, in German Offenlegungsschrift (German Published Specification) No. 2,839,646, European Patent Specification No. 21,676, Belgian Patent Specification No. 849,118 and in S. Yamamoto et al. Heterocycles 8, 282 (1977) and M. Narisada et al. L. Med. Chem. 22, 757 (1979), Heterocycles 7, 839 (1977).

The compounds of the general formula (7) can also be prepared by processes analogous to other processes which are known from the literature, such as are described, for example, in Japanese Patent Specification No. 55 047,687, Dutch Patent Specification No. 7,313,896 or by Y. Hamashima et al., Tetrahedron Lett. (1979) 4943).

Possible starting substances for optically active oxazolinoazetidinones of the general formula (1S,5R) (4) and (1R,5S) (4) are, where relevant, the compounds of the general formula (9) of corresponding configuration.

Examples from the literature exist for the synthesis of both enantiomers of the compounds of the general formula (9) in which R[1] is phenyl: (1S,5R) (9): S. Yamamoto et al., Tetrahedron Lett. (1981) 3089, (1R,5S) (9): Y. Hamashima et al., Tetrahedron Lett. (1979) 2595.

Other compounds (9) can be prepared analogously.

If, for example, methyl 2-[(1S,5R)-3-benzyl-7-oxo-4-oxa-2,6-diazabicyclo[3.2.0]hept-2-en-6-yl)]-3-methylbut-3-enoate (9a) is used, the course of the reaction for the preparation of the compounds (4) can be represented by the following equation:

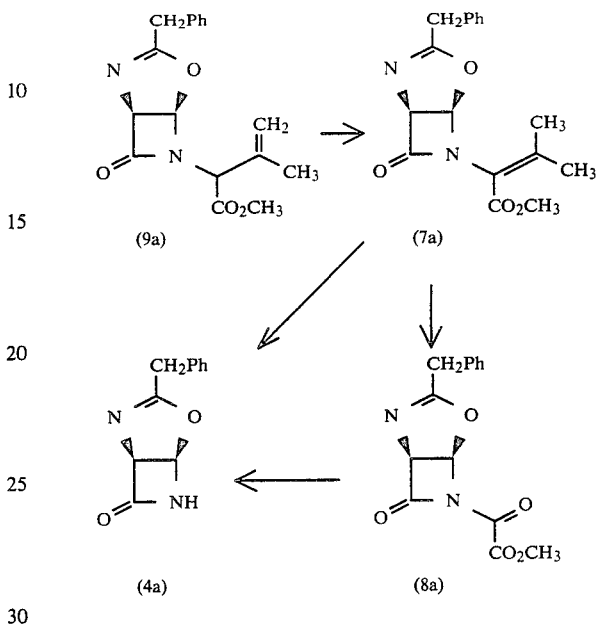

Possible reagents in the reaction of compounds of the formula (9) to give compounds of the formula (7) are all the customary organic and inorganic bases. Preferred bases include the alkali metal hydroxides, alkali metal carbonates, alkali metal amides and organic amines. Potassium carbonate, triethylamine, diisopropylethylamine, pyridine, dimethylaniline, diethylamine, 1,5-diazabcyclo(5.4.0)undec-5-ene (DBU), DBN and ammonia are particularly suitable.

Possible diluents are all the inert organic solvents, and organic bases and water. Preferred diluents include ethyl acetate, tetrahydrofuran, methylene chloride, dichloroethane, dichlorobenzene, toluene, ethylamine and dimethylamine. The isomerization is in general carried out at temperatures between −50° and +50° C., but preferably between 0° C. and room temperature.

Possible reagents in the reaction of compounds of the formula (7) to give compounds of the formula (8) are all the customary oxidizing agents which are capable of splitting an olefinic double bond in the manner described.

Sodium periodate, osmium tetroxide, oxygen-ozone and mixtures thereof may be mentioned as preferred. Possible diluents are all the inert organic solvents. Preferred solvents include ethyl acetate, ethanol, methanol, tetrahydrofuran, methylene chloride, dichloroethane, toluene and dioxane, and mixtures thereof.

If necessary, a reducing agent is to be added in this reaction step before the working up. Inorganic or organic sulphur compounds can preferably be used here. Diorganyl sulphides, such as, for example, dimethyl sulphide, are particularly suitable.

The reactions are in general carried out between −80° C. and +50° C., but preferably between −80° C. and 0° C.

Possible reagents in the reaction of compounds of the formula (7) to give compounds of the formula (4) are all the customary oxidizing agents. Those which first lead to dihydroxylation of the conjugated double bond are preferably used. If appropriate, the reaction mentioned can be carried out by processes analogous to known processes (E. G. Brain et al., J.C.S. Chem. Comm. (1972) 229, German Offenlegungsschrift (German Published Specification) No. 2,156,352, A. K. Bose et al., Tetrahedron 37, 2321 (1981) and J. S. Wells et al., J. Antibiot. 35 189 (1982)).

Preferred oxidizing agents are potassium permanganate, sodium periodate, osmium tetroxide and mixtures thereof.

Oxidizing agents such as lead tetraacetate, copper-II acetate or N-halogeno-succinimides and -phthalimides can likewise be used. Possible solvents are all those solvents which have a solvolytic action and effect such detachment of the oxidized butenoate radical from the β-lactam. Solvents which may be mentioned in particular are: water, methanol, ethanol, acetone, pyridine, triethylamine, dimethylformamide and mixtures thereof. If appropriate, basic or acid auxiliaries may be used. Preferred auxiliaries include potassium carbonate, buffer solutions, organic amines, such as triethylamine or pyridine, sulphuric acid, silicic acid or silica gel, and organic sulphonic acids. The reaction is preferably carried out between −40° C. and +80° C.

Possible diluents in the reaction of compounds of the formula (8) to give compounds of the formula (4) are all the solvents which have a solvolytic action and are suitable for effecting solvolysis of the oxamide structure, such as is described analogously, for example, in European Patent Specification No. 21,676, German Offenlegungsschrift (German Published Specification) No. 2,839,646 and by R. D. G. Cooper et al., J. Am. Chem. Soc. 94, 1021 (1972).

Preferred solvents include organic alcohols, primary amines and water and mixtures thereof with inert solvents. Methanol and other alcohols with 1–5C atoms may be mentioned in particular. If appropriate, basic or acid auxiliaries may be added to assist in the reaction. Preferred auxiliaries include alkali metal alcoholates, alkali metal carbonates, buffer solutions, organic amines, carboxylic acids, sulphonic acids and inorganic proton acids. Auxiliaries which may be mentioned in particular are: sodium methanolate, potassium carbonate, weakly basic or weakly acid buffer solutions, sulphuric acid, perchloric acid, phosphoric acid, silicic acid and silica gel. The reaction is preferably carried out between −30° C. and +70° C., but in particular between 0° C. and room temperature.

Compounds of the general formula (5) in which X and $R^2$ have the stated meaning and Y represents hydrogen ($H_2$) can be prepared from 4-halogeno-acetoacetic acid esters analogously to known processes (European Patent No. 67 409; K. Clauss, Liebigs Ann. Chem. 494 (1980)); 4-halogeno acetoacetic acid esters can be reacted with O- and S-nucleophiles in a known manner. The 4-hydroxy- and 4-mercapto-acetoacetic acid esters required can be liberated by splitting off the protective groups in question (T. W. Greene, Protective Groups in Organic Syntheses, J. Wiley+Sons (1981)).

The compounds of the general formula (5), in which X and $R^2$ have the stated meaning and Y represents diazo ($N_2$), can be prepared analogously to known processes (R. W. Ratcliffe et al. Tetrahedron Lett. (1980) 31; U.S. Pat. No. 4,310,538), from compounds of the general formula (5) in which X and $R^2$ have the stated meaning and Y represents hydrogen ($H_2$), by diazo transfer reactions.

The compounds of the general formula (6) can be prepared by processes which are known from the literature or by analogous processes [R. A. Earl et al., Organic Syntheses 60, 81 (1981)]. Methods of hydrating triple bonds in β-lactam chemistry are likewise known [S. Ikegami et al., Tetrahedron Lett. 2875 (1982)].

A feature of the invention is the stereoselective ring-opening of N-unsubstituted oxazolinoazetidinones of the general formula (4) with nucleophiles of the general formulae (5) and (6).

It is to be described as exceptionally surprising that this reaction can be carried out on N-unsubstituted oxazolinoacetidinones. The spectrum of the possible target compounds is widened decisively by the N-substituents which are not present from the beginning. Thus, according to the invention, in contrast to the prior art, both monofunctional and bifunctional reagents, which facilitate subsequent fusing of rings onto the azetidinone, can be used.

A further feature of the invention is the fusing of sulphur-containing or oxygen-containing 6-membered rings onto the azetidinone by an intramolecular insertion reaction of a carbene obtained from a diazoacetic acid ester into the N—H bond of the azetidinone.

Such fusing reactions to form 6-membered rings have been disclosed for $X=CH_2$ (U.S. Pat. No. 4,174,316; and T. N. Salzmann et al. Tetrahedron Lett. (1980) 1193) and for $X=O$ (European Pat. No. 81,824). This type of reaction has not yet been described for $X=S$.

The process sequence according to the invention has a number of advantages. The synthesis according to the invention is convergent and thus two finished molecule parts are effectively combined, that is to say in the nature of a building block principle.

All the processes known at present for the preparation of 3-hydroxy-cephalosporin derivatives or oxacephem derivatives are multi-stage linear syntheses in which all the reaction steps are carried out in the presence of the preformed β-lactam ring, which is of decisive disadvantage in view of the known sensitivity of the β-lactam ring. Compared with conversion syntheses, linear syntheses also have a significant strategic disadvantage (S. Warren, Designing Organic Syntheses, J. Wiley+Sons, 1978, page 201).

Building units of the general formula (4) can be reacted to a large number of conceivable bicyclic β-lactam compounds, depending on the choice of the reaction partner. As a result of this strategy, the number of operations to be carried out in the presence of the sensitive β-lactam ring is restricted to a minimum.

If, for example, (1R,5S)-3-phenyl-4-oxa-2,6-diazabicyclo[3.2.0]hept-2-en-7-one and tert.-butyl 4-mercaptoacetoacetate are used as starting materials, the course of the reaction can be represented by the following equation:

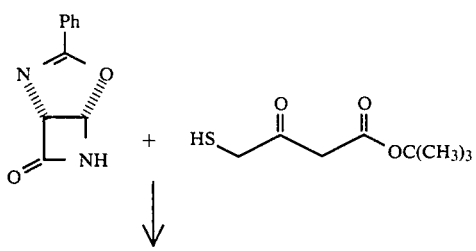

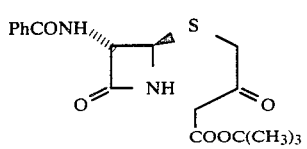

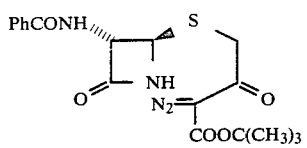

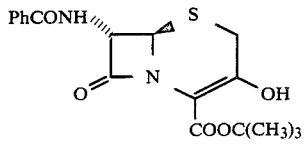

If, for example, (1R,5S)-3-phenyl-4-oxa-2,6-diazabicyclo[3.2.0]hept-2-en-7-one and 4-nitrobenzyl 4-hydroxy-2-butinoate are used as starting materials, the course of the reaction can be represented by the following equation:

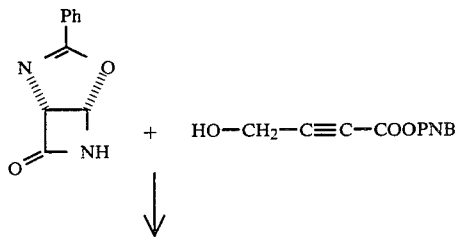

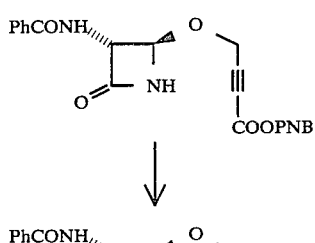

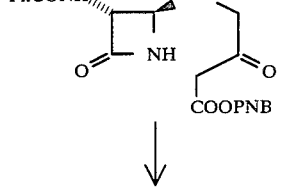

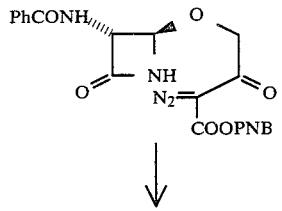

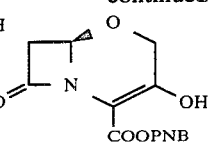

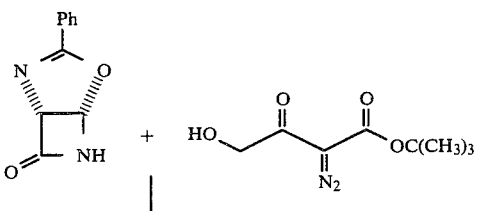

If, for example, (1R,5S)-3-phenyl-4-oxa-2,6-diazabicyclo[3.2.0]hept-2-en-7-one and tert.-butyl-2-diazo-4-hydroxy-3-oxo-butanoate are used as starting materials the course of the reaction can be represented by the following equation:

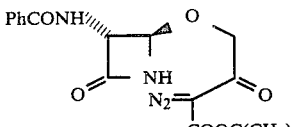

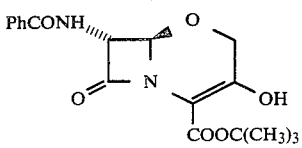

In the compounds of the general formulae (1), (2), (3), (4), (7), (8) and (9), $R^1$ as optionally substituted alkyl represents a straight-chain, branched or cyclic hydrocarbon radical with preferably 1–7 C atoms. The alkyl radicals can optionally be unsaturated and can optionally be monosubstituted or disubstituted by halogen, preferably chlorine, hydroxyl, amino, carboxyl, carbamoyl or mesyl, or by optionally substituted aryl or heteroaryl which is defined in more detail below. Radicals such as methyl, halogenomethyl, tert.-butyl, cyclohexyl and cyclohexadinyl may be mentioned in particular here.

$R^1$ has optionally substituted aryl preferably stands for phenyl, which can be substituted, preferably mono- or di-substituted, but in some cases also tri-substituted, by methyl, ethyl, aminomethyl, hydroxyl, methoxy, ethoxy, carbamyloxy, acetoxy, amino, mesylamino, methylamino, aminosulphonylamino, amidino, mesyl, methylsulphinyl, methoxycarbonyl, carbamyl, sulpho, methylthio, silyl, silyloxy or halogen, preferably chlorine or bromine.

Optionally substituted aralkyl represents combinations of the meanings given under aryl and alkyl. Radicals which may be mentioned in particular are: benzyl, p-hydroxybenzyl, p-aminobenzyl, α-aminobenzyl, α,4-diaminobenzyl, α-amino-4-hydroxybenzyl, α-carboxybenzyl, α-carboxy-4-hydroxybenzyl and bis-(trimethylsilyl)-protected α-carboxy-4-hydroxybenzyl.

Optionally substituted heteroaryl represents all the unsaturated 5-membered or 6-membered heterocyclic rings which have 1-4 hetero-atoms, contain oxygen, nitrogen and/or sulphur atoms in the ring and can be unsubstituted or, preferably, mono-, di- or tri-substituted by methyl, ethyl, hydroxyl, oxo, amino, imino, mesyl, mesylamino, silyl, carboxy, carbamyl, acetyl or halogen, preferably chlorine or bromine.

An unsaturated optionally substituted heterocyclic ring preferably is the furyl, methylfuryl, thienyl, methylthienyl, 2-aminothiazolyl, thiazolyl, methylisoxazolyl, isoxazolyl, pyridyl, 2-aminopyridyl, pyrimidyl, pyrazolyl, uracyl, thiadiazolyl, tetrazolyl or pyranyl group.

Optionally substituted heteroalkyl represents combinations of the meanings given as preferred under alkyl and heteroaryl. Furylmethyl, thienylmethyl, 2-aminothiazolylmethyl, thiazolylmethyl, aminopyridylmethyl, 1-methyl-1-H-tetrazol-5-yl-thiomethyl, 2-aminothiazolylmethoxyiminomethyl and 1-(2-aminothiazolyl)-1-propenyl may be mentioned in particular here.

Optionally substituted aryloxyalkyl, heteroaryloxyalkyl and alkoxyalkyl represent the abovementioned meanings, which carry an oxygen bridge in the form of an ether function in the alkyl part or between the alkyl and aryl or heteroaryl part. Radicals which may be mentioned in particular are: phenoxymethyl, 4-hydroxyphenoxymethyl, α-aminophenoxymethyl, α-amino-4-hydroxy-phenoxymethyl, methoxymethyl, tert.-butoxymethyl, thienyloxymethyl, α-aminothienyloxymethyl, furyloxymethyl and α-aminofuryloxymethyl.

Optionally substituted alkoxy or aryloxy represents the alkyl or aryl radicals defined above which are bonded directly via an oxygen bridge. Radicals which may be mentioned in particular are: methoxy, ethoxy, tert.-butoxy, phenoxy, benzyloxy, diphenylmethyloxy, 4-nitrobenzyloxy and 4-methoxybenzyloxy.

Optionally substituted alkylthio or arylthio represents the alkyl or aryl radicals defined above, which are bonded directly via a sulphur bridge. Radicals which may be mentioned in particular are: methylthio, ethylthio, tert.-butylthio, phenylthio, benzylthio, diphenylmethylthio and 4-nitrobenzylthio.

Optionally substituted arylthioalkyl, heteroarylthioalkyl and alkylthioalkyl represent the abovementioned meanings, which carrying a sulphur bridge in the form of a thioether function in the alkyl part or between the alkyl and aryl or heteroaryl part. Radicals which may be mentioned in particular are: phenylthiomethyl, 4-hydroxyphenylthiomethyl, α-aminophenylthiomethyl, 2-methyl-1-thia-3,4-diazol-5-yl-thiomethyl, methylthiomethyl and tert.-butylthiomethyl.

The following radicals R$^1$ may be mentioned as examples:

| Radical R$^1$ |
| --- |
| H |
| CH$_3$ |
| C(CH$_3$)$_3$ |
| H$_2$C=CH$_2$ |

—CH$_2$—Ph

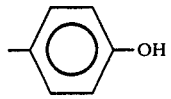

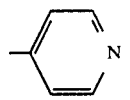

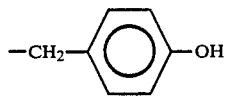

—CH$_2$—O—Ph

—CH(NH$_2$)—O—Ph

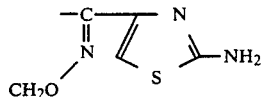

—CH$_2$—O—CH$_3$

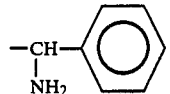

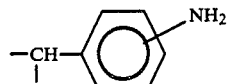

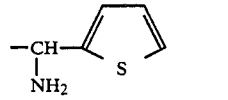

—CH$_2$—S—(tetrazole-N-CH$_3$)

—CH$_2$—S—(thiadiazole-CH$_3$)

—CH$_2$=S—CH$_2$

—SC(CH$_3$)$_2$

| Radical R¹ |
|---|
|  |
| 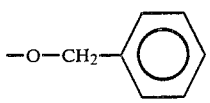 |
| 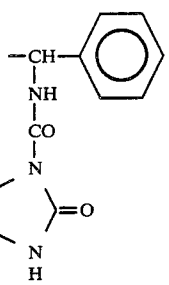 |
| 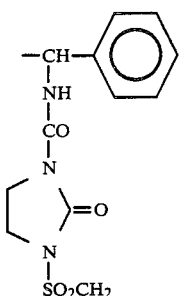 |
|  |

In compounds of the general formulae (1), (2), (3), (5) and (6), the expression carboxy-protective group in the meaning of R² represents the protective groups known in β-lactam chemistry, for example an optionally substituted benzyl, diphenylmethyl or triphenylmethyl group, a silyl group or an optionally substituted ethyl or allyl group. Groups such as benzyl, 2-nitrobenzyl, 4-nitrobenzyl, 4-methoxybenzyl, 2,4-dimethoxybenzyl, diphenylmethyl, triphenylmethyl, trichloroethyl, chloroethyl, cyanoethyl, trimethylsilylethyl and dimethylethyl may be mentioned in particular.

A pharmaceutically useful ester radical R² here preferably means compatible ester radicals which are easily split in vivo to give free carboxyl groups (R²=H).

Such ester radicals R² are well known in the field of β-lactam antibiotics. In most cases, they improve the absorption properties of the β-lactam compound. In addition, the nature of R² should be such that it imparts pharmaceutically acceptable properties to a compound of the formula (1) and liberates pharmaceutically acceptable fragments when split in vivo. Examples of such groups R² are to be found in DE-OS (German Published Specification) No. 2,517,316.

Possible catalysts in the preparation according to the invention of compounds of the general formula (1) from compounds of the general formula (2) are complexes or salts of transition metals or elemental transition metals. Preferred catalysts are complexes of copper, rhodium and palladium, such as, for example, [Cu(acac)₂], Rh₂(OAc)₄ and Pd(OAc)₂, and in addition CuSO₄ and Cu powder. Rhodium-II acetate [Rh₂(OAc)₄] may be mentioned in particular.

[acac=acetylacetonate; OAc=acetate].

In general, up to molar amounts of the catalyst can be employed. However, catalytic amounts of between 0.1 and 5 mol % are preferably used.

Possible diluents are all the inert organic solvents. Preferred solvents include aromatic solvents, such as benzene, toluene and the like, but also tetrahydrofuran and methylene chloride. The reaction is in general carried out at temperatures between 40° and 120° C., but preferably between 70° and 90° C., in the course of 0.5–5 hours.

Instead of using catalysts, the reaction according to the invention can also be carried out by irradiation of compounds of the general formula (2) with a light source of wavelength ≧300 nm. Possible solvents here are all the inert organic solvents. Preferred solvents include benzene, toluene, carbon tetrachloride, methylene chloride, ether, tetrahydrofuran and dioxane. The photocyclisation is in general carried out between −20° and +30° C. in the course of 0.5 to 3 hours.

Possible reagents in the preparation according to the invention of compounds of the general formula (2) from compounds of the general formula (3) are all the azides which are capable of effecting the reaction according to the invention. Examples of azides include optionally substituted methane-, benzene- or naphthalenesulphonyl azides. Toluenesulphonyl azide, 4-dodecylbenzenesulphonyl azide and 4-carboxybenzenesulphonyl azide may be mentioned in particular. Possible bases are all the customary inorganic and organic bases. Preferred bases include alkali metal carbonates, alkali metal amides and organic amines. Triethylamine, diethylamine, diisopropylethylamine, pyrimidine, dimethylaniline, 1,5-diazabicyclo[5.4.0]undec-5-ene (DBU) and DBN are particularly suitable.

Possible diluents are all the inert organic solvents and organic bases. Preferred diluents include tetrahydrofuran, methylene chloride, acetone, acetonitrile, dimethoxyethane and dioxane. Acetonitrile may be mentioned in particular. The diazotisation is in general carried out between −20° and +30° C. in the course of 1 to 48 hours.

In the preparation according to the invention of compounds of the general formula (2) by the linking of compounds of the general formulae (4) and (5) in which X and R² have the stated meaning and Y represents diazo (N₂), the two reaction partners can be used in equivalent quantities. It is however also possible for one partner—most advantageously the compound of the general formula (5)—to be used in excess. In certain cases the compound of the general formula (5) may even serve as the solvent. Possible acid catalysts are protonic acids, for example, trifluoroacetic acid, trifluoromethane sulfphonic acid, perchloric acid, tetrafluorboric acid, hydrochloric acid, squaric acid, p-toluenesulphonic acid, camphorsulphonic acid, polyphosphoric acid or lewis acids, for example boron trifluoride, zinc-II chloride, aluminium chloride, tin-IV chloride, mercury-II chloride, silicon tetrachloride, tin-II chloride, titanium-IV chloride, antimony-V chloride, iron-III chloride and antimony-III chloride, and also trimethylsilyl trifluoromethanesulphonate and trimethylsilyl trifluoroacetate as well as acid ion exchangers and silica gel. In general, up to molar amounts of the acid catalyst may be added. However, the reaction is preferably carried out in the presence of catalytic amounts (that is to say 1-25 mol %).

Possible diluents are all the inert solvents. Examples of solvents include dimethoxyethane, diglyme, triglyme, tetrahydrofuran, dioxane, diethyl ether, t-butyl methyl ether, methylene chloride, carbon tetrachloride, 1,2-dichloroethane, 1,1,2-trichloroethane, trichloroethylene, chlorobenzene, dichlorobenzene, chloroform, ethyl acetate, toluene, cyclohexane, acetonitrile and nitromethane. The reaction is in general carried out between −30° and +50° C., but preferably at room temperature, in the course of 0.1 to 10 hours. The rate of reaction depends on the amount of catalyst used.

The two reaction partners can be used in equivalent amounts in the preparation according to the invention of compounds of the general formula (3) by linking compounds of the general formulae (4) and (5), in which X and $R^2$ have the stated meaning and Y represents hydrogen ($H_2$). However, it is also possible for one partner—most advantageously the compound of the general formula (5)—to be used in excess. In certain cases, the compound of the general formula (5) may even serve as the solvent. Possible acid catalysts are proton acids, for example trifluoroacetic acid, trifluoromethanesulphonic acid, perchloric acid, tetrafluoboric acid, hydrochloric acid, squaric acid p-toluenesulphonic acid, camphorsulphonic acid and polyphosphoric acid, and Lewis acids, for example boron trifluoride, zinc-II chloride, aluminium chloride, tin-IV chloride, mercury-II chloride, silicon tetrachloride, tin-II chloride, titanium-IV chloride, antimony-V chloride, iron-III chloride and antimony-III chloride, and also trimethylsilyl trifluoromethanesulphonate and trimethylsilyl trifluoroacetate as well as acid ion exchangers and silica gel. In general, up to molar amounts of the acid catalyst may be added. However, the reaction is preferably carried out in the presence of catalytic amounts (that is to say 1-10 mol %).

Possible diluents are all the inert solvents. Examples of solvents include dimethoxyethane, diglyme, triglyme, tetrahydrofuran, dioxane, diethyl ether, t-butyl methyl ether, methylene chloride, carbon tetrachloride, 1,2-dichloroethane, 1,1,2-trichloroethane, trichloroethylene, chlorobenzene, dichlorobenzene, chloroform, ethyl acetate, toluene, cyclohexane, acetonitrile and nitromethane. The reaction is in general carried out between −30° and +50° C., but preferably at room temperature, in the course of 0.1 to 10 hours. The rate of reaction depends on the amount of catalyst used.

The preparation according to the invention of compounds of the general formula (3) by reacting compounds of the general formula (4) with compounds of the general formula (6) is carried out under the same conditions as have been described above for the reaction of compounds of the general formula (4) with compounds of the general formula (5). The triple bond of the intermediate compound thereby formed must subsequently still be hydrated. Processes which are known from the literature can be used for hydration of the triple bond, such as those which have been described, for example, by S. Ikegami et al., Tetrahedron Lett. 2875 (1982). This procedure is furthermore illustrated in detail in the examples.

The following examples serve to further describe the invention, without restricting it:

EXAMPLE 1

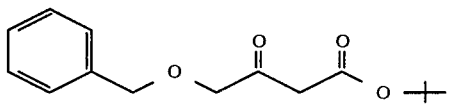

tert.-Butyl 4-benzyloxyacetoacetate

A solution of 64.9 g=62.1 ml (0.6 mol) of benzyl alcohol in 50 ml of tetrahydrofuran was added dropwise to an ice-cooled suspension of 18.0 g (0.6 mol) of sodium hydride (80% strength in parafin oil) in 150 ml of anhydrous tetrahydrofuran in the course of 1 hour with ice-cooling. Thereafter, the mixture was subsequently stirred at room temperature for 0.5 hour. A solution of 57.8 g (0.3 mol) of tert.-butyl 4-chloroacetoacetate in 50 ml of tetra-hydrofuran was added dropwise at 0° C. in the course of 1 hour. The ice-bath was removed and the reaction mixture was stirred at room temperature for a further hour and neutralized by careful addition of 0.5N HCl, with cooling (pH control).

The mixture was extracted several times with ether and the combined ether extracts were washed with water and dried over $MgSO_4$. Evaporation of the ether in vacuo gave an oil, which was purified by chromatography on 1.7 kg of silica gel (toluene:ethyl acetate 95:5). 41.7 g (53%) of tert.-butyl 4-benzyloxyacetoacetate were obtained, $R_F$: 0.47 (toluene:ethyl acetate 9:1).

$^1$H-NMR (200 MHz, $CDCl_3$) δ 1.50 (s, 9H, $C(CH_3)_3$), 3.48 (s, 2H, $CH_2$), 4.18 (s, 2H, $CH_2$), 4.63 (s, 2H, $CH_2$) and 7.40 (s, 5H, Ph).

IR ($CHCl_3$) 1740-1710 (c=0, β-keto ester) and 1656 cm$^{-1}$ (C=C, enol form).

$C_{15}H_{20}O_4$ (264.3) calculated: C 68.2, H 7.6; found: C 68.2, H 7.6.

EXAMPLE 2

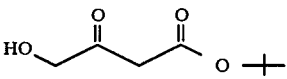

tert.-Butyl 4-hydroxyacetoacetate

A mixture of 963 mg (5 mmol) of tert.-butyl 4-benzyloxyacetoacetate and 200 mg of palladium (10% on charcoal) in 50 ml of methanol was stirred at room temperature under a hydrogen atmosphere (1 atmosphere) for 1.5 hours. The catalyst was filtered off washed with a little methylene chloride. The filtrate solution was evaporated in vacuo and the residue was filtered through 3 g of neutral aluminum oxide (methylene chloride). The solvent was evaporated off in vacuo and the oil which remained was dried under a high vacuum. 567 mg (65% of tert.-butyl 4-hydroxyacetoacetate were obtained, and were used immediately for further reactions.

$R_F$: 0.31 (toluene:ethyl acetate 3:2)

$^1$H-NMR (200 MHz, $CDCl_3$) 1.50 (s, 9H, $C(CH_3)_3$), 3.05 (bs, 1H, OH), 3.43 (s, 2H, $CH_2$) and 4.38 (bs, 2H, $CH_2$).

$C_8H_{14}O_4$ (174.2) calculated: C 55.16, H 8.10; found: C 55.2, H 8.3.

EXAMPLE 3

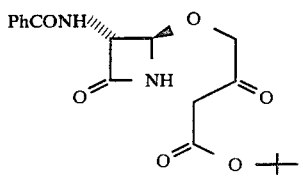

tert.-Butyl 4-[3(R)-benzoylamino-2-azetidinon-4(R)-yloxy]acetoacetate 30 ul of boron trifluoride etherate were added to a suspension of 216 mg (1.15 mmols) of (1R, 5S)-3-phenyl-4-oxa-2,6-diazabicyclo[3.2.0]hept-2-en-7-one and 400 mg (2.3 mmols) of freshly prepared tert.-butyl 4-hydroxyacetoacetate in 4 ml of anhydrous tetrahydrofuran at room temperature. After a short time a clear, light yellow solution formed, which was stirred for 0.5 hour at room temperature. It was then poured into dilute NaHCO$_3$ solution. The mixture was extracted with methylene chloride, washed with water and dried over magnesium sulphate. After the solvent had been evaporated off in vacuo and the residue had been chromatographed on 60 g of silica gel (toluene:ethyl acetate 1:3), 128 mg (31%) of tert.-butyl 4-[3(R)-benzoylamino-2-azetidinon-4(R)-yloxy]acetoacetate were obtained as colorless crystals, melting point: 142° C., R$_F$: 0.36 (toluene:ethyl acetate 1:4), $[\alpha]_D^{20} = 32.24°$ (0.955 percent in CHCl$_3$).

IR (KBr): 3320 (NH), 1763 (C=O, β-lactam), 1738 (C=O, ketone), 1720 (C=O, ester), 1656 and 1524 cm$^{-1}$ (amide).

$^1$H-NMR (200 MHz, CDCl$_3$) δ 1.45 (s, 9H, C(CH$_3$)$_3$), 3.43 (s, 2H, COCH$_2$COOR), 4.50 (AB, J=15 Hz, 2H, OCH$_2$CO), 4.78 (dd, J=1 Hz, 8 Hz, 1H, H-3), 5.15 (d, J=1 Hz, 1H, H-4), 7.13 (s, 1H, NH), 7.3–7.6 (m, 4H, Ph, NH), 7.8 (m, 2H, ortho-benzoyl-H).

C$_{18}$H$_{22}$N$_2$O$_6$ (362.4) calculated: C 59.66, H 6.12, N 7.73; found: C 59.5, H 5.2, N 7.6.

EXAMPLE 4

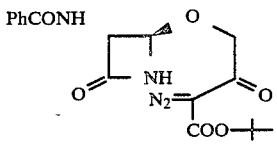

tert.-Butyl 4-[3(R)-benzoylamino-2-azetidinon-4(R)-yloxy]-2-diazo-3-oxo-butyrate 258 μl (1.85 mmols—3.75 equivalents) of triethylamine were added dropwise to a solution, cooled to 0° C., of 184 mg (0.5 mmol) of tert.-butyl 4-[3(R)-benzoylamino-2-azetidinon-4(R)-xyloxy]-acetoacetate and 100 mg (0.55 mmol) of freshly prepared p-toluenesulphonic acid azide in 10 ml of anhydrous acetonitrile. The cooling bath was removed and the mixture was stirred at room temperature for 1.5 hours. The reaction mixture was then concentrated in vacuo and chromatographed on 8 g of silica gel (toluene:ethyl acetate 35:65). 186 mg (96%) of tert.-butyl 4-[3(R)-benzoylamino-2-azetidinon-4(R)-yloxy]-2-diazo-3-oxo-butyrate were obtained as light crystals, melting point: 127° C. (decomposition), R$_F$: 0.30 (toluene:ethyl acetate 35:65), $[\alpha]_D^{20} = -15.4°$ (0.867 percent strength in CHCl$_3$).

IR (KBr): 3307 (NH); 2154 (N$_2$), 1786 (C=O, β-lactam), 1699 (C=O, ester), 1643 (amide I) and 1527 cm$^{-1}$ (amide II).

$^1$H-NMR (250 HMz, CDCl$_3$) δ 1.54 (s, 9H, C(CH$_3$)$_3$), 4.77 (dd, J=7 Hz, ~1 Hz, 1H, H-3), 4.89 (AB, J=17 Hz, 2H, CH$_2$O), 5.26 (d, J=~1 Hz, 1H, H-4), 7.1–7.5 (m, 5H, NH, NH, Ph) and 7.8 (m, 2H, o-benzoyl-H).

C$_{18}$H$_{20}$N$_4$O$_6$ (388.4) calculated: C 55.67, H 5.19, N 14.43; found: C 55.7, H 5.4, N 13.9.

EXAMPLE 5

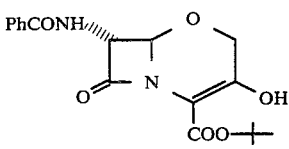

tert.-Butyl (6R, 7R)-7-benzoylamino-3-hydroxy-8-oxo-5-oxa-1-azabicyclo[4.2.0]oct-2-ene-2-carboxylate (a) A suspension of 341 mg (0.88 mmol) of tert.-butyl 4-[3(R)-benzoylamino-2-azetidinon-4(R)-yloxy]-2-diazo-3-oxo-butyrate and 0.5 mg of rhodium-II acetate in 18 ml of anhydrous benzene was freed from oxygen for 10 minutes by passing in dry nitrogen.

The reaction mixture was then heated at 80° C. for 1 hour, whereupon the solid starting material gradually dissolved. The mixture was allowed to cool and the catalyst was removed by filtration (kieselguhr) and washed with methylene chloride.

The solvent was evaporated off in vacuo and the residue was chromatographed on 20 g of silica gel (toluene:ethyl acetate 35:65). 260 mg (82%) of tert.-butyl (6R, 7R)-7-benzoylamino-3-hydroxy-8-oxo-5-oxa-1-azabicyclo[4.2.0]oct-2-ene-2-carboxylate were obtained as a colorless rigid form, R$_F$: 0.36 (toluene:ethyl acetate 3:7).

IR (KBr): 3324 (OH, NH), 1771 (C=O, β-lactam), 1655 (β-keto ester, enol form), 1655 and 1532 cm$^{-1}$ (amide).

$^1$H-NMR (250 MHz, CDCl$_3$) δ 1.59 (s, 9H, C(CH$_3$)$_3$), 4.42 (AB, J=17.5 Hz, 2H, CH$_2$O), 4.93 (d, J=7.5 Hz, 1H, H-7), 5.05 (s, 1H, H-6), 7.05 (d, J=b 7.5 Hz, 1H, NH) 7.3–7.6 (m, 3H, Ph) and 7.8 (m, 2H, ortho-benzoyl-H).

C$_{18}$H$_{21}$N$_2$O$_6$ (361.4) calculated: C 59.83, H 5.86, N 7.75; found: C 59.8, H 5.6, N 7.9.

(b) An anhydrous and degassed solution of 78 mg (0.2 mmol) of tert.-butyl 4-[3(R)-benzoylamino-2-azetidinon-4-(R)-yloxy]-2-diazo-3-oxo-butyrate in 25 ml of benzene:tetrahydrofuran 3:1 was irradiated in a nitrogen atmosphere at 20° C. for 1 hour with a 450 W mercury vapour lamp with a Pyrex filter. The solvent was evaporated off in vacuo and the residue was purified by chromatography on 8 g of silica gel (toluene:ethyl acetate 35:65). 12 mg (17%) of the title compound were obtained as a colorless rigid foam.

The physical data were identical to those of the compound prepared according to method (a).

EXAMPLE 6

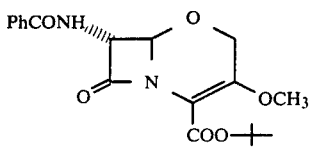

tert.-Butyl (6R, 7R)-7-benzoylamino-3-methoxy-8-oxo-5-oxa-1-azabicyclo[4.2.0]oct-2-ene-2-carboxylate A solutin of diazomethane in ether was added to a solution of 260 mg (0.72 mmol) of tert.-butyl (6R, 7R)-7-benzoylamino-3-hydroxy-8-oxo-5-oxa-1-azabicyclo[4.2.0]oct-2-ene-2-carboxylate in 3 ml of anhydrous methylene chloride at room temperature until a yellow coloration remained. The solvent and excess diazomethane were then evaporated off in vacuo and the residue was chromatographed on 18 g of silica gel (toluene-:ethyl acetate 2:3). 169 mg (62%) of the title compound were obtained as a colorless rigid foam.

$R_f$: 0.53 (toluene:ethyl acetate 1:4).

IR (KBr): 3354 (NH), 1775 (C=O, β-lactam), 1722 (C=O, ester, 1650 and 1531 cm$^{-1}$ (amide).

$^1$H-NMR (250 MHz, CDCl$_3$) δ 1.53 (s, 9H, C(CH$_3$)$_3$), 3.78 (s, 3H, OCH$_3$), 3.36, 4.48 (d, J=18 Hz, 2H, CH$_2$O), 5.00 (s, 1H, H-6), 5.04 (d, J=b 7.5 Hz, 1H, H-7), 7.3–7.6 (m, 4H, Ph, NH) and b 7.85 (m, 2H, o-benzoyl-H).

C$_{19}$H$_{22}$N$_2$O$_6$ (374.4) calculated: C 60.95, H 5.92, N 7.48; found: C 60.9, H 5.8, N 7.3.

EXAMPLE 7

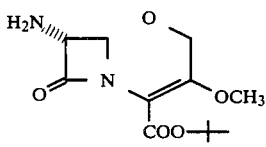

tert.-Butyl (6R, 7R)-7-amino-3-methoxy-8-oxo-5-oxa-1-azabicyclo[4.2.0]oct-2-ene-2-carboxylate 0.4 ml (5 mmols—2.5 equivalents) of pyridine and then, all at once, 0.83 g (4 mmols—2 equivalents) of phosphorus pentachloride were added to a solution, cooled to −20° C., of 749 mg (2 mmols) of tert.-butyl (6R, 7R)-7-benzoylamino-3-methoxy-8-oxo-5-oxa-1-azabicyclo[4.2.0]oct-2-ene-2-carboxylate in 3.7 ml of anhydrous methylene chloride. The mixture was stirred at 0° C. for 10 minutes and at +15° C. for 1 hour and cooled to −60° C., 12.2 ml of precooled anhydrous methanol were added rapidly and the mixture was subsequently stirred at room temperature for 30 minutes. It was then cooled to −15° C., 1.6 ml of distilled diethylamine was added and stirring was continued for 10 minutes at about −10° C. and the mixture was poured into ice-cold saturated NaHCO$_3$ solution, for working up. The mixture was extracted several times with methylene chloride and the extract was washed with water and dried over MgSO$_4$. The solvent was evaporated off in vacuo and the residue was chromatographed on 60 g of silica gel (ethyl acetate:acetone 85:15). 158 mg (29%) of the title compound were obtained as a light rigid foam, $R_f$: 0.33 (ethyl acetate:acetone 85:15).

IR (KBr): 1771 (C=O, β-lactam), 1720 (C=O, ester), 1603 cm$^{-1}$ (O-C=C).

$^1$H-NMR (250 MHz, CDCl$_3$) δ 1.5 (s, 9H, C(CH$_3$)$_3$), 1.75 (bs, 2H, NH$_2$), 3.77 (s, 3H, OCH$_3$), 4.06 (s, 1H, H-7), 4.45 (AB, J=17 Hz, 2H, CH$_2$O) and 4.79 (s, 1H, H-6).

EXAMPLE 8

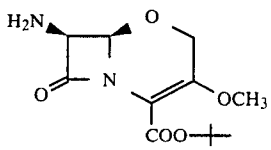

tert.-Butyl (6R, 7S)-7-amino-3-methoxy-8-oxo-5-oxa-1-azabicyclo[4.2.0]oct-2-ene-2-carboxylate 7.7 g of molecular sieve 3 Å and, after a few minutes, 2.3 ml (23.5 mmols—4.7 equivalents) of anhydrous trichloroacetaldehyde were added to a solution of 1.35 g (5 mmols) of tert.-butyl (6R, 7R)-7-amino-3-methoxy-8-oxo-5-oxa-1-azabicyclo[4.2.0]oct-2-ene-2-carboxylate in 81 ml of benzene. The mixture was heated at the boiling point for 2.5 hours, with stirring, cooled, filtered rapidly and concentrated in vacuo. The residue was dissolved in 23 ml of anhydrous tetrahydrofuran and the solution was cooled to −40° C. 0.89 ml (5.1 mmols—1.02 equivalents) of ethyldiisopropylamine was added and the mixture was stirred at −40° C. and then allowed to warm to 0° C. At this temperature, a precooled solution of 2.18 mg of potassium borohydride in 35 ml of 50 percent strength aqueous tetrahydrofuran was added rapidly and the mixture was stirred for 5 minutes. The reaction was then quenched with a mixture of 38 ml of 2N HCl and 17 ml of acetonitrile at 0° C. and the mixture was subsequently stirred for a further 2 hours. For working up, the mixture was poured into saturated NaHCO$_3$ solution and extracted with methylene chloride and the extract was washed with water and dried over MgSO$_4$. After the solvent had been evaporated off in vacuo and the residue had been chromatographed on 120 g of silica gel (ethyl acetate-:acetone 6:4), 372 mg (28%) of the title compound were obtained as a colorless rigid foam.

IR (KBr): 1773 (C=O, β-lactam), 1718 (C=O, ester) and 1611 cm$^{-1}$ (O-C=C).

$^1$H-NMR (250 MHz, CDCl$_3$) δ1.5 (s, 9H, C(CH$_3$)$_3$), 1.68 (bs, 2H, NH$_2$), 3.75 (s, 3H, OCH$_3$), 4.44, 4.56 (AB, J=17.5 Hz, CH$_2$O), 4.45 (d, J=4.5 Hz, H-7) add 3H, 4.97 (d, J=4.5 Hz, 1H, H-6).

EXAMPLE 9

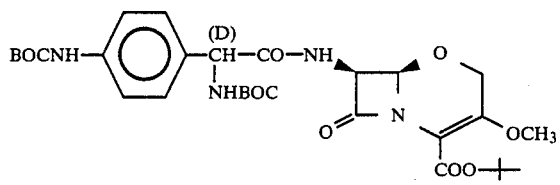

tert.-Butyl (6R, 7S)-7-[(2R)-1-tert.-butoxycarbonylamino-2-(4-tert.-butoxycarbonlyaminophenyl)-acetamido]-3-methoxy-8-oxo-5-oxa-1-azabicyclo[4.2.0]oct-2-ene-2-carboxylate 235 μl (1.35 mmols) of ethyldiisopropylamine and 105 μl (1.35 mmols) of methanesulphonyl chloride were successively added dropwise to a solution, cooled to −50° C., of 495 mg (1.35 mmols) of N,N'-bis-(tert.-butoxycarbonyl)-4-amino-D-phenylglycine(-[α]$_D^{20}$=−106.5°, 1.033 percent in methanol) in 8 ml of anhydrous methylene chloride. The mixture was stirred at −50° C. for 45 minutes and a solution of 354 mg (1.31 mmols) of tert.-butyl (6R, 7S)-7-amino-3-methoxy-8-oxo-5-oxa-1-azabicyclo[4.2.0]oct-2-ene-2-carboxylate and 235 μl (1.35 mmol of ethyldiisoproplamine in 6.5 ml of anhydrous methylene chloride was then added dropwise. The mixture was stirred at −50° C. for a further 15 minutes and was then allowed to warm to −10° C. For working up, the mixture was poured into a mixture of 100 ml of ice-water and 50 ml of methylene chloride, extracted with methylene chloride, washed with NaHCO₃ solution and water and dried over MgSO₄. After the solvent had been evaporated off and the residue chromatographed on 45 g of silica gel (toluene:ethyl acetate 1:1), 422 mg (52%) of the title compound were obtained as a colorless rigid foam.

IR (KBr): 1783 (C=O, β-lactam), 1725 (C=O, ester), 1680 and 1520 cm⁻¹ (amide).

¹H-NMR (250 MHz, CDCl₃) δ1.42, 1.50, 152, 1.60 (s, 27H, C(CH₃)₃), 3.76 (s, 3H, OCH₃), 4.34, 4.43 (AB, J=16 Hz, 2H, CH₂O), 5.0 (d, J=4 Hz, 1H, H-6), 5.17 (bs, 1H, CH), 5.6 (dd, J=4 Hz, 9.5 Hz, 2H, H-7, NH), 6.55 (bs, 2H, NH) and 7.3, 7.5 (d, J=8.5 Hz, 4H, H$_{aromatic}$).

EXAMPLE 10

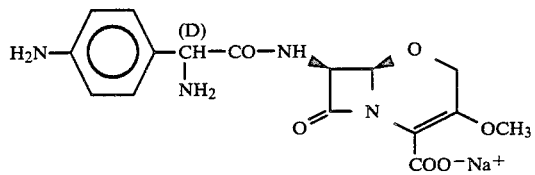

Sodium (6R, 7S)-7-[(2R)-2-amino-2-(4-aminophenyl)acetamido]-3-methoxy-8-oxo-5-oxa-1-azabicyclo[4.2.0]oct-2-ene-2-carboxylate A solution of 414 mg (0.67 mmol) of tert.-butyl (6R, 7S)-7-[(2R)-2-tert.-butyoxycarbonylamino-2-(4-tert.-butoxycarbonylaminophenyl)-acetamido]-3-methoxy-8-oxo-5-oxa-1-azabicyclo[4.2.0]oct-2-ene-2-carboxylate in 10 ml of anhydrous trifluoracetic acid was stirred at room temperature for 1 hour. 15 ml of benzene were then added and the mixture was evaporated in vacuo. The residue was triturated with ether and the powder thereby formed was filtered off with suction, washed with ether and dissolved in 20 ml of doubly-distilled water. The aqueous phase was extracted several times with ether, freed from ether residues in vacuo, filtered through a column containing Amberlite IRA-68 (acetate form) and eluted with 200 ml of water. After the eluate had been freeze-dried, 166 mg (65%) of the title compound were obtained in a purity of 96% (high pressure liquid chromatography).

IR (KBr): 3500-2900 (b) and 1764 cm⁻¹ (C=O, β-lactam).

¹H-NMR (250 MHz, DMSO δ3.74 (s, 3H, OCH₃), 4.39, 4.46 (AB, J=17 Hz, CH₂O), 4.2–4.6 (m, NH₂, CH) add. 7H, 5.05 (d, J=4 Hz, 1H, H-6), 5.43 (dd, J=4 Hz, 9 Hz, 1H, H-7), 6.54, 7.09 (d, J=10 Hz, 4H, H$_{aromatic}$) and 8.82 (d, J=9 Hz, 1H, NH).

EXAMPLE 11

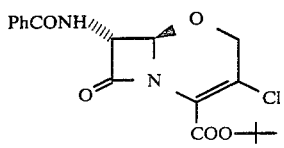

tert.-Butyl (6R, 7R)-7-benzoylamino-3-chloro-8-oxo-5-oxa-1-azabicyclo[4.2.0]oct-2-ene-2-carboxylate 30.5 ml (32.6 mmols—1.5 equivalents) of phosphorus trichloride were added dropwise to a solution, cooled to 0° C., of 7.82 g (21.7 mmols) of tert.-butyl (6R, 7R)-7-benzoylamino-3-hydroxy-8-oxo-5-oxa-1-azabicyclo[4.2.0]oct-2-ene-2-carboxylate in 430 ml of anhydrous dimethylformamide. The cooling bath was removed and the mixture was stirred at room temperature for 2 hours.

For working up, the mixture was poured into a mixture of methylene chloride and ice-water and extracted with methylene chloride (2×) and the extract was washed with NaHCO₃ solution and water (2×) and dried over MgSO₄. After the solvent had been evaporated off in vacuo and the residue had been chromatographed on 340 g of silica gel (toluene:ethyl acetate 7:3), 2.47 g (30%) of the title compound were obtained as a colorless rigid foam.

IR (KBr): 3360 (NH), 1787 (C=0,β-lactam), 1721 (C=0, ester), 1650 and 1518 cm³¹ ¹ (amide).

¹H-NMR (250 MHz, CDCl₃) δ1.55 (s, 9H, C(CH₃)₃), 4.35–4.48 (AB, J=17.5 Hz, 2H, CH₂O), 4.92 (s, 1H, H-6), 5.18 (d, J=7.5 Hz, 1Hz, H-7), 7.3–7.6 (m, 4H, Ph, NH) and 7.9 (m, 2H, o-benzoyl-H).

EXAMPLE 12

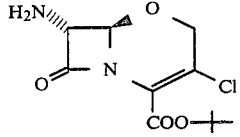

tert.-Butyl (6R, 7R)-7-amino-9-chloro-8-oxo-5-oxa-1-azabicyclo[4.2.0]oct-2-ene-2-carboxylate As described for Example 7, 308 mg (36%) of the title compound are obtained as a light powder from 1.19 g (3.15 mmols) of tert.-butyl (6R, 7R)-7-benzoylamino-3-chloro-8-oxo-5-oxa-1azabicyclo[4.2.0]oct-2-ene-2-carboxylate after chromatography of the crude product on 93 g of silica gel (toluene:ethyl acetate 1:4).

IR (KBr): 3387 (NH₂ as.), 3320 (NH₂ sym), 1780 (C=0, β-lactam), 1726 (C=0, ester and 1609 cm⁻¹ (C=C).

¹H-NMR (250 MHz, CDCl₃) δ1.53 (s, 9H, C(CH₃)₃), 1.9 (bs, 2H, NH₂), 4.13 (s, 1H, H-7), 4.4, 4.48 (AB, H=17 Hz, 2H, CH₂O) and 4.86 (s, 1H, H-6).

EXAMPLE 13

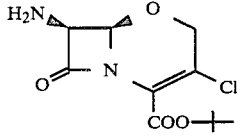

tert.-Butyl (6R, 7S)-7-amino-3-chloro-8-oxo-5-oxa-1-azabicyclo[4.2.0]oct-2-ene-2-carboxylate As described for Example 8, 837 mg (35%) of the title compound were obtained as a light-colorless rigid foam from 2.39 g (8.7 mmols) of tert.-butyl (6R, 7R)-7-amino-3-chloro-8-oxo-5-oxa-1-azabicyclo[4.2.0]oct-2-ene-2-carboxylate and chromatography of the crude product on 80 g of silica gel (ethyl acetate).

IR (KBr): 3399 (NH$_2$as.), 3320 (NH$_2$ sym.), 1787 (C=O, β-lactam), 1728 (C=O, ester) and 1606 cm$^{-1}$ (C=C).

$^1$H-NMR (250 MHz, CDCl$_3$) δ1.5 (s, C(CH$_3$)$_3$), 1.75 (bs, NH$_2$), add. 11H, 4.48, 4.54 (AB, J=16 Hz, 2H, CH$_2$O), 4.59 (d, J=4.5 Hz, 1H, H-7), 5.1 (d, J=4.5 Hz, 1H, H-6).

EXAMPLE 14

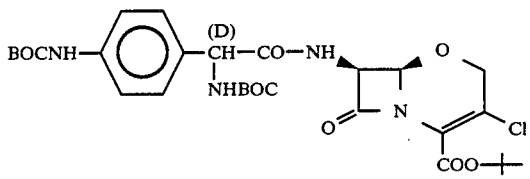

tert.-Butyl (6R, 7S)-7-[(2R)-2-tert.-butoxycarbonylamino-2-(4-tert.-butoxycarbonylaminophenyl)acetamido]-3-chloro-8-oxo-5-oxa-1-azabicyclo[4.2.0]oct-2-ene-2-carboxylate As described for Example 9, 805 mg (38%) of the title compound were obtained as a colorless rigid foam from 934 mg (3.4 mmols) of tert.-butyl (6R, 7S)-7-amino-3-chloro-8-oxo-5-oxa-1-azabicyclo[4.2.0]oct-2-ene-2-carboxylate and 1.28 g (3.5 mmol) of N,N'-bis(tert.-butoxycarbonyl)-4-amino-D-phenylglycine, after chromatography on 155 g of silica gel (toluene:ethyl acetate 7:3).

IR (KBr): 1803 (C=O, β-lactam), 1730 (C=O, ester), 1680 and 1520 cm$^{-1}$ (amide).

$^1$H-NMR (250 MHz, CDCl$_3$) δ1.42, 1.50, 1.53, 1.58 (s, 27H, C(CH$_3$)$_3$), 4.4 (AB, J=17 Hz, 2H, CH$_2$O), 5.1 (d, J=4 Hz, H-6), 5.15 (bs, CH), add. 2H, 5.5 (bs, 1H, NH), 5.7 (dd, J=4, 10 Hz, 1H, H-7), 6.52, 6.54 (bs, 2H, NH), 7.3 and 7:5 (d, J=9 Hz, 4H, H$_{aromatic}$).

EXAMPLE 15

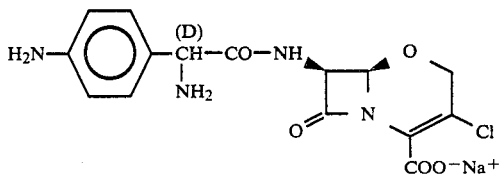

Sodium (6R, 7S)-7-[(2R)-2-amino-2-(4-aminophenyl)-acetamido]-3-chloro-8-oxo-5-oxa-1-azabicyclo[4.2.0]oct-2-ene-carboxylate As described for Example 10, 361 mg (76%) of the title compound were obtained in a purity of 89% (high pressure liquid chromatography) from 760 mg (1.22 mmols) of tert.-butyl (6R, 7S)-7-[(2R)-2-tert.-butoxycarbonylamino-2-(4-tert.-butoxycarbonylaminophenyl)acetamido]-3-chloro-8-oxo-5-oxa-1-azabicyclo[4.2.0]oct-2-ene-carboxylate.

IR (KBr): 3500-2900 (b), 1776 (C=O, β-lactam), 1680 and 1517 (amide) and 1609 cm$^{-1}$ (COONa).

$^1$H-NMR (250 MHz, DMSO) δ3.5-4.5 (b, NH$_2$), 4.1, 4.37 (AB, J=17 Hz, CH$_2$O), 4.8 (m, CH), add. 7H, 5.11 (d, J=4 Hz, 1H, H-6), 5.49 (dd, J=4 Hz, 9 Hz, 1H, H-7), 6.54, 7.11 (d, J=9.5 Hz, 4H, H$_{aromatic}$) and 9.14 (d, J=9 Hz, 1H, NH).

EXAMPLE 16

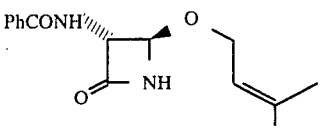

3(R)-Benzoylamino-4-(R)-[3-methyl-2-butenyloxy]-2-azetidinone 181 mg (0.96 mmol—1.2 equivalents) of anhydrous tin-II chloride (dried by fusing briefly under a high vacuum) were added all at once, at 0° C., to a suspension of 150 mg (0.78 mmol) of (1R, 5S)-3-phenyl-4-oxa-2,6-diazabicyclo[3.2.0]hept-2-en-7-one in 1.3 ml of anhydrous methlene chloride and 0.81 ml (7.8 mmols—10 equivalents) of 3-methyl-2-buten-1-ol. The cooling bath was removed and a clear solution was formed after a few minutes. The reaction mixture was stirred for a further 15 minutes at room temperature, poured into dilute NaHCO$_3$ solution and extracted with methylene chloride and the extract was washed with water and dried over MgSO$_4$. After the solvent had been evaporated off in vacuo and the residue had been filtered on 5 g silica gel (toluene:ethyl acetate 3:7), 153 mg (70%) of the title compound were obtained as colorless crystals, melting point: 92° C., R$_f$: 0.38 (toluene:ethyl acetate 3:7).

IR (KBr): 1775 (C=O, β-lactam), 1667 (C=O, amide), 1633 (C=C) and 1529 cm$^{-1}$ (amide II-band).

$^1$H-NMR (200 MHz, CDCl$_3$) δ1.70, 1.77 (s, 6H, CH$_3$), 4.18 (m, 2H, —OCH$_2$—CH=), 4.74 (dd, J=9 Hz, 1 Hz, 1H, H-3), 5.23 (d, J=1 Hz, 1H, H-4), 5.38 (m, 1H, —CH=), 6.78 (s, 1H, NH), 7.18 (d, J=9, Hz, 1H, NH), 7.4–7.6 (m, 3H, C$_6$H$_5$) and 7.8 (m, 2H, o—C$_6$H$_5$).

MS (70 ev): m/e=274 (M+); calculated: 274.32

C$_{15}$H$_{18}$N$_2$O$_3$ (274.3) calculated: C 65.7, H 6.6, N 10.2; found: C 65.4, H 6.5, N 10.0.

EXAMPLE 17

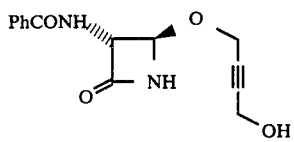

4-[3(R)-Benzoylamino-2-azetidion-4-(R)-yloxy]-2-butin-1-ol

100 μl of boron trifluoride etherate were added to a suspension of 941 mg (5 mmols) of (1R, 5S)-3-phenyl-4-oxa-2,6-diazabicyclo[3.2.0]hept-2-en-7-one and 861 mg (10 mmols—2equivalents) of 2-butin-1,4-diol in 20 ml of anhydrous tetrahydrofuran at room temperature. The mixture was stirred at room temperature for 2 hours, a clear solution initially being formed, from which a solid precipitate later separated out. The precipitate was filtered off with suction and the filtrate solution was poured into dilute NaHCO$_3$ solution. The mixture was extracted with methylene chloride and the extract was washed with water and dried over MgSO$_4$. After the solvent had been evaporated off in vacuo and the residue had been chromatographed on 100 g of silica gel (toluene:ethyl acetate 1:9), 74 mg (8.2%) of 4-[3(R)-benzoylamino-2-azetidinon-4(R)-yloy]-2-butin-1-ol were obtained as a colorless rigid foam.

$R_F$=0.21 (toluene:ethyl acetate 1:9).

IR (CHCl$_3$): 3351 (NH, OH), 1779 (C=O, β-lactam), 1664 and 1528 cm$^{-1}$ (amide).

$^1$H-NMR (200 MHz, DMSO) δ4.11 (d, J=6 Hz, 2H, CH$_2$OH), 4.32 (AB, J=17 Hz, 2H, CH$_2$O), 4.65 (dd, J=9 Hz, 1 Hz, 1H, H-3), 5.21 (d, J=1 Hz, H-4), 5.21 (t, J=6 Hz, CH$_2$OH) together 2H, 7.5–7.6 (m, 3H, Ph), 7.75 (m, 2H, o-benzoyl-H), 9.02 (s, 1H, NH) and 9.18 (d, J=9 Hz, 1H, NH).

EXAMPLE 18

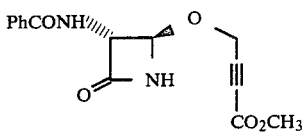

Methyl 4-[3(R)-benzoylamino-2-azetidinon-4(R)-xyloxy]-2-butinoate (a) 0.41 ml of boron trifluoride etherate was added to a suspension of 4.70 g (25 mmols) of (1R, 5S)-3-phenyl-4-oxa-2,6-diazabicyclo[3.2.0]hept-2-en-7-one and 14.3 g (125 mmols—5 equivalents) of methyl 4-hydroxy-2-butinoate (R. A. Earl, Organic Synthese 60, 81) in 40 ml of anhydrous methylene chloride at room temperature. The mixture was stirred at room temperature for 1 hour, whereupon a clear solution formed. The solution was then poured into dilute NaHCO$_3$ solution, the mixture was extracted with methylene chloride and the extracts were washed with water and dried over MgSO$_4$. After the solvent had been evaporated off in vacuo and the residue had been filtered on 120 g of silica gel (toluene:ethyl acetate 2:3), 4.74 g (63%) of methyl 4-[3(R)-benzoylamino-2-azetidinon-4(R)-yloxy]-2-butinoate were obtained as colorless crystals, melting point: 142°–143° C, $R_F$: 0.29 (toluene:ethyl acetate 2:3), [α]$_D^{20}$=18.37° (1.0345 percent in acetone).

IR (CHCl$_3$): 2240 (C≡C), 1784 (C=O, β-lactam), 1717 (C=O, ester) and 1662 cm$^{-1}$ (C=O, amide).

$^1$H-NMR (250 MHz, DMSO) δ3.70 (s, 3H, COOCH$_3$), 4.54 (AB, J=15 Hz, 2H, CH$_2$O), 4.66 (dd, J=8 Hz, 1 Hz, 1H, H-3), 5.24 (d, J=1 Hz, 1H, H-4), 7.5–7.65 (m, 3H, Ph), 7.9 (m, 2H, ortho-benzoyl-H), 9.08 (s, 1H, NH) and 9.18 (d, J=8 Hz, 1H, NH).

C$_{15}$H$_{14}$N$_2$O$_5$ (302.3) calculated: C 59.60, H 4.67, N 9.27; found: C 59.2, N 4.7, N 9.2.

(b) 114 mg (0.6 mmol—1.2 equivalents) of anhydrous tin-II chloride were added to a suspension of 94 mg (0.5 mmol) of (1R, 5S)-3-phenyl-4-oxa-2,6-diazabicyclo[3.2.0]hept-2-en-7-one and 290 mg (2.5 mmol) of methyl 4-hydroxy-2-butinoate in 0.8 ml of anyhydrous methylene chloride at 0° C. The mixture was then stirred at room temperature for 1 hour, whereupon a clear solution formed. After working up and purification as described under (a), 35 ml (23%) of the title compound of melting point: 142°–142.5° C. were obtained, the physical data of this compound being identical to those of the substance prepared according to method (a).

EXAMPLE 19

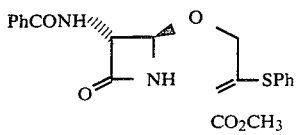

Methyl E,Z-4[3(R)-benzoylamino-2-azetidinon-4(R)-yloxy]3-phenylthio-2-butenoate

113 μl (1.1 mmols) of thiophenol and 153 μl of triethylamine were added successively to a solution, cooled to 0° C., of 302 mg (1 mmol) of methyl 4-[3(R)-benzoylamino-2-azetidinon-4(R)-xyloxy]-2-butinoate in 5 ml of THF. The ice-bath was removed and the mixture was stirred at room temperature for 3 hours. It was then poured into saturated NaHCO$_3$ solution and extracted with methylene chloride and the extract was washed with water and dried over MgSO$_4$. The solvent was evaporated off in vacuo and the crude product was crystallized from methylene chloride/ether. 280 mg (68%) of the title compound were obtained as a mixture of double-bond isomers; melting point: 178° C., $R_F$: 0.48 (toluene:ethyl acetate 1:4).

IR (KBr): 3317 (NH), 1807 (C=O, β-lactam), 1704 (C=O, ester), 1642 and 1533 (amide) and 1602 cm$^{-1}$ (S—C=C).

$^1$H-NMR (250 MHz, DMSO) δ3.61, 3.63 (s, 3H, COOCH$_3$), 3.95 (s, 2H, CH$_2$O), 4.48 (d, J=8 Hz, 1H, H-3), 4.78 (s, 1H, H-4), 6.14, 6.16 (s, 1H, —CH=C), 7.3–7.6 (m, 8H, pH), 7.85 (m, 2H, o-benzoyl-H), 8.85 (s, 1H, NH-β-lactam) and 9.05, 9.10 (d, J=8 Hz, 1H, PhCONH).

C$_{21}$H$_{20}$N$_2$O$_5$S (412.5) calculated: C 61.15, H 4.89, N 6.79, S 7.77; found: C 61.1, H 4.9, N 6.8, S 7.7.

EXAMPLE 20

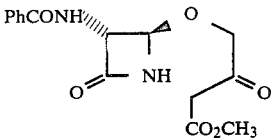

Methyl 4-[3(R)-benzoylamino-2-azetidinon-4(R)-yloxy]acetoacetate 690 mg (5 mmols) of N-bromoacetamide were added all at once to a solution, cooled to 0° C., of 412 mg (1 mmol) of methyl E,Z-4[3(R)-benzoylamino-2-azetidinon-4(R)-yloxy]-3-phenylthio-2-butenoate in 13 ml of dioxane:water 10:1. The light brown solution was stirred at 0° C., for 2 hours and quenched at this temperature with 12 ml of saturated Na$_2$SO$_3$ solution. The mixture was stirred at 0° C. for a further 40 minutes, allowed to come briefly to room temperature and extracted 3 times with ethyl acetate. The extract was washed with water and dried over MgSO$_4$ and the crude product was purified by chromatography on 7.5 g of silica gel (toluene:ethyl acetate 1:4). The title compound was obtained as a foam, $R_F$: 0.22 (toluene:ethyl acetate 1:4).

IR (CHCl$_3$): 3328 (NH), 1777 (C=O, β-lactam), 1737 (C=O, ketone), 1725 (C=O, ester), 1658 and 1525 cm$^{-1}$ (amide).

$^1$H-NMR (250 MHz, CDCl$_3$) δ3.53 (s, 2H, COCH$_2$COOR), 3.71 (s, 3H, COOCH$_3$), 4.46, 4.58 (AB, J=17

Hz, 2H, CH$_2$O), 4.77 (d, J=7.5 Hz, 1H, H-3), 5.14 (s, 1H, H-4) and 7.4–7.7 (m, 7H, Ph, NH).

EXAMPLE 21

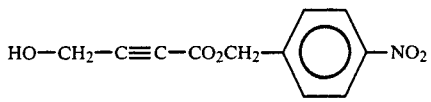

4-Nitrobenzyl 4-hydroxy-2-butinoate

A solution of 3.3 ml (23.2 mmols) of tetrahydro-2-(2-propinyloxy)-2H-pyran [R. A. Earl et al., Organic Syntheses 60, 81 (1981)] in 23 ml of anhydrous tetrahdrofuran was added dropwise to 7.8 ml (23.2 mmols) of a 3 molar solution of ethyl-magnesium bromide in ether at room temperature in the course of 30 minutes. The mixture was then subsequently stirred at room temperature for 1.5 hours. This solution was added dropwise to a well-stirred solution, cooled to −20° C., of 5.0 g (23.2 mmol) of 4-nitrobenzyl chloroformate in 25 ml of tetrahydrofuran in the course of 1.5 hours. The mixture was then subsequently stirred at −15° C. for 30 minutes and at 0° C. for 1.5 hours, and was then left to stand at 0° C. for 12 hours, whereupon the magnesium salts crystallized out. The salts were filtered off, with exclusion of moisture, and washed two times with a little toluene. The filtrate solution was washed 5 times with saturated NaCl solution and dried over MgSO$_4$. The solvent was evaporated off in vacuo, the residue was dissolved in 25 ml of anhydrous methanol and the solution was stirred with 1 ml of the ion exchanger Dowex-50-X4 (H$^+$ form, prewashed with anhydrous methanol) at room temperature for 1 hour. The ion exchanger was separated off, the filtrate solution was concentrated in vacuo and, finally, the residue was dried under a high vacuum. The treatment with the ion exchanger was repeated as described above. The crude product was chromatographed on 300 g of silica gel (toluene:ethyl acetate 4:1) and 2.07 g (38%) of 4-nitrobenzyl 4-hydroxy-2-butinoate were obtained as colorless crystals, melting point: 93°–94° C., R$_F$: 0.27 (toluene:ethyl acetate 4:1).

IR (KBr): 3475 (OH), 2235 (—C≡C—), 1690 (C=O, ester), 1524 (NO$_2$, as.) and 1348 cm$^{-1}$ (NO$_2$, sym.).

$^1$H-NMR (200 MHz, DMSO) δ4.30 (d, J=6 Hz, 2H, CH$_2$OH), 5.38 (s, 2H, CH$_2$—), 5.63 (t, J=6 Hz, 1H, CH$_2$OH), 7.68 (d, J=20 Hz, 2H, H$_{aromatic}$) and 8.15 (d, J=20 Hz, 2H, H$_{aromatic}$).

C$_{11}$H$_9$NO$_5$ (235.2) calculated: C 56.2, H 3.9, N 6.0; found: C 56.2, H 3.9, N 6.1.

EXAMPLE 22

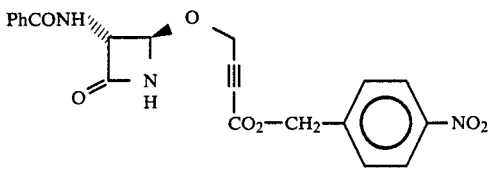

4-Nitrobenzyl 4-[3(R)-benzoylamino-2-azetidinon-4(R)-yloxy]-2-butinoate

10 μl of boron trifuloride etherate were sprayed into a stirred suspension of 376 mg (2mmols) of (1R, 5S)-3-phenyl-4-oxa-2,6-diazabicyclo[3.2.0]hept-2-en-7-one and 941 mg (4 mmols) of 4-nitrobenzyl 4-hydroxy-2-butinoate in 8 ml of anhydrous tetrahydrofuran at room temperature. After a short time, a clear, light yellow solution formed, and was stirred at room temperature for 0.5 hour. Thereafter, the solution was poured into dilute NaHCO$_3$ solution, the mixture was extracted with methylene chloride and the extract was washed with water and dried over MgSO$_4$. After the solvent had been evaporated off in vacuo and the residue had been chromatographed on 60 g of silica gel (toluene-:ethyl acetate 35:65), 557 mg (66%) of 4-nitrobenzyl 4-[3(R)-benzoylamino-2-azetidinon-4(R)-yloxy]-2-butinoate were obtained as a colorless rigid foam.

R$_F$: 0.55 (ethyl acetate), [α]$_D^{20}$=−35.28° (0.5 percent in CHCl$_3$).

IR (KBr): 3330 (NH), 2244 (C≡C), 1780 (C=O, β-lactam), 1715 (C=O, ester), 1651 and 1524 (amide), 1524 (NO$_2$-as) and 1350 cm$^{-1}$ (NO$_2$-sym.).

$^1$H-NMR (250 MHz, CDCl$_3$) δ4.54 (AB, J=16 Hz, 2H, CH$_2$O), 4.69 (d, J=9 Hz, 1H, H-3), 5.28 (s, 2H, CH$_2$-benzyl), 5.34 (s, 1H, H-4), 7.08 (s, 1H, NH), 7.4–7.6, 7.8 (m, Ph, NH), 7.51, 8.21 (d, J=9.5 Hz, AB-4-nitrobenzyl) together 10H.

C$_{21}$H$_{17}$N$_3$O$_7$ (423.39) calculated: C 59.58, H 4.05, N 9.92; found: C 58.8, H4.0, N 9.8.

EXAMPLE 23

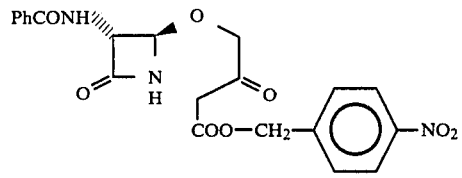

4-Nitrobenzyl 4[3(R)-benzoylamino-2-azetidinon-4(R)-yloxy]-acetoacetate 0.15 ml (1.43 mmols—1.1 equivalents) of thiophenol and 0.2 ml (1.43 mmols—1.1 equivalents) of triethylamine were successively added to a solution, cooled to 0° C., of 551 mg (1.3 mmols of 4-nitrobenzyl 4-[3(R)-benzoylamino-2-azetidinon-4-(R)-yloxy]-2-butinoate in 6.6 ml of tetrahydrofuran. The mixture was stirred at room temperature for 3 hours, poured into saturated NaHCO$_3$ solution and extracted several times with methylene chloride and the extracts were dried over MgSO$_4$.

The solvent was evaporated off in vacuo and the residue was dissolved in 15 ml of dioxane:water 10:1. 1.44 g (10.41 mmols—8 equivalents) of N-bromoacetamide were added all at once at 0° C. and the mixture was subsequently stirred at this temperature for 5.5 hours. Thereafter, 15 ml of cold, saturated Na$_2$SO$_3$ solution were added and the mixture was subsequently stirred at 0° C. for 40 minutes. Thereafter, the mixture was allowed to warm briefly to room temperature, and was then extracted 4 times with ethyl acetate. The organic extracts were washed with water and dried over MgSO$_4$. The solvent was evaporated off in vacuo, a little methylene chloride was added to the residue and, after crystallization, the product was triturated with ether. 479 mg (83%) of the title compound were obtained as colorless crystals, melting point: 138°–139° C., R$_F$: 0.27 (toluene:ethyl acetate 1:4).

IR (KBr): 3338 (NH), 1174 (C=O, β-lactam, 1740 (C=O, ketone), 1720 (C=O, ester), 1641 and 1512 (amide) and 1346 cm$^{-1}$ NO$_2$-sym.).

$^1$H-NMR (200 MHz, DMSO) δ 3.75 (s, 2H, COCH$_2$COOR), 4.43 (s, 2H, CH$_2$O), 4.65 (d, J=9 Hz, 1H, H-3), 5.18 (s, 1H,

H-4), 5.30 (s, 2H, CH$_2$-benzyl), 7.45–7.9 (m, Ph), 7.65, 8.25 (d, J=9.5 Hz, AB-4-nitrobenzyl) together 9H, 9.00 (s, 1H, NH) and 9.14 (d, J=9 Hz, 1H, PhCONH).

C$_{21}$H$_{19}$N$_3$O$_8$ (441.4) calculated: C 57.14, H 4.34, N 9.52; found: C 56.9, H 4.3, N 9.2.

EXAMPLE 24

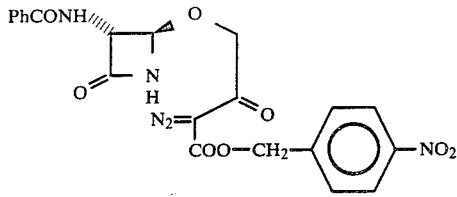

4-Nitrobenzyl 4-[3(R)-benzoylamino-2-azetidinon-4(R)-yl-oxy]-2-diazo-3-oxo butanoate 0.75 ml (5.4 mmols—3.6 equivalents) of triethylamine was added dropwise to a suspension, cooled to 0° C., of 662 mg (1.5 mmols) of 4-nitrobenzyl 4-[3(R)-benzoylamino-2-azetidinon-4(R)-yloxy]-acetoacetate and 395 mg (1.74 mmol—1.16 equivalents) of 4-carboxybenzenesulphonyl azide in 15 ml of anhydrous acetonitrile. The cooling bath was removed and the mixture was subsequently stirred at room temperature for 1 hour. 100 ml of ethyl acetate were then added and the insoluble precipitate was filtered off with suction and discarded. The filtrate solution was evaporated in vacuo and ether was added to the residue. 540 mg (77%) of the title compound were obtained as colorless crystals, melting point: 135° C., R$_F$: 0.44 (toluene:ethyl acetate 1:9).

IR (KBr): 3317 (NH), 2154 (N$_2$), 1789 (C=O, β-lactam), 1709 (C=O, ester, 1660 and 1521 cm$^{-1}$ (amide).

$^1$H-NMR (200 MHz, DMSO) δ 4.64 (dd, J=9 Hz, 1 Hz, 1H, H-3), 4.72 (s, 2H, CH$_2$O), 5.27 (d, J=1 Hz, 1H, H-4), 5.44 (s, 2H, CH$_2$-benzyl), 7.5–7.9 (m,Ph) 7.71, 8.26 (d, J=9.5 Hz, AB-4-nitrobenzyl) together 9H, 9.00 (s; 1H, NH), 9.15 (d, J=9 Hz, 1H, PhCONH).

C$_{21}$H$_{17}$N$_5$O$_8$ (467.39) calculated: C 54.0, H 3.7, N 15.0; found: C 53.6, H 3.8, N 14.8.

EXAMPLE 25

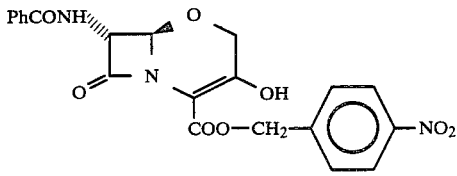

4-Nitrobenzyl (6R, 7R)-7-benzoylamino-3-hydroxy-8-oxo-5-oxa-1-azabicyclo[4.2.0]oct-2-ene-2-carboxylate As described for Example 5, 230 mg (47.6%) of the title compound, R$_F$: 0.37 (ethyl acetate), were obtained from 510 mg (1.1 mmols) of 4-nitrobenzyl 4[3(R)-benzoyl-amino-2-azetidinon-4(R)-yloxy]-2-diazo-3-oxo-butanoate, after crystallization of the crude product from ether.

IR (KBr): 3320 (b, OH, NH), 1776 (C=O, β-lactam), 1652 (β-ketoester, enol form), 1660 and 1525 cm$^{-1}$ (amide).

$^1$H-NMR (200 MHz, DMSO) δ 4.38 (AB, J=18 Hz, 2H, CH$_2$O), 4.98 (d, J=9 Hz, 1H, H-7), 5.20 (s, 1H, H-6), 5.45 (s, 2H, CH$_2$-benzyl), 7.5–8.2 (m, 9H, H$_{aromatic}$) and 9.24 (d, j=9 Hz, 1H, NH).

EXAMPLE 26

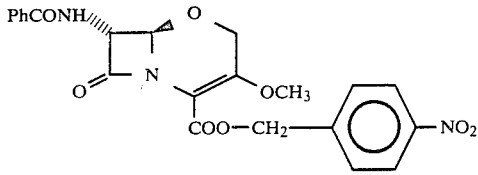

4-Nitrobenzyl (6R, 7R)-7-benzoylamino-3-methoxy-8-oxo-5-oxa-1-azabicyclo[4.2.0]oct-2-ene-2-carboxylate As described for Example 6, 75 mg (56%) of the title compound were obtained as a colorless powder, R$_F$: 0.33 (toluene:ethyl acetate 3:7), from 130 mg (0.3 mmol) of 4-nitrobenzyl (6R, 7R)-7-benzoylamino-3-hydroxy-8-oxo-5-oxa-1-azabicyclo[4.2.0]oct-2-ene-2-carboxylate, after chromatography of the crude product on 15 g of silica gel (toluene:ethyl acetate 35:65).

IR (KBr): 3361 (NH), 1771 (C=O, β-lactam), 1724 (C=O, ester), 1650 and 1517 (amide), 1605 (C=C) and 1349 cm$^{-1}$ (NO$_2$-sym.).

$^1$H-NMR (250 MHz, CDCl$_3$) δ 3.85 (s, 3H, OCH$_3$), 4.50, 4.63 (AB, J=17 Hz, 2H, CH$_2$O), 4.97 (d, J=8 Hz, 1H, H-7), 5.10 (s, 1H, H-6), 5.30, 5.45 (AB, J=15 Hz, CH$_2$-benzyl), 7.11 (d, J=8 Hz, 1H, NH) 7.4–7.9 (m, Ph) and 7.65, 8.24 (AB, J=10 Hz, 4-nitrobenzyl), together 9H.

EXAMPLE 27

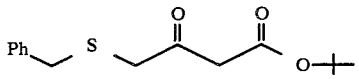

tert.-Butyl 4-benzylthioacetoacetate 7.04 ml (60 mmols) of benzylmercaptan were slowly added dropwise to a suspension of 1.8 g (60 mmols) of sodium hydride (80% in parafin oil) in 50 ml of anhydrous tetrahydrofuran at room temperature. Thereafter, the mixture was subsequently stirred for 15 minutes and then cooled to 0° C. A solution of 10.57 g (55 mmols) of tert.-butyl 4-chloroacetoacetate in 20 ml of tetrahydrofuran was added at this temperature in the course of 1 hour. The ice-bath was removed and the mixture was stirred at room temperature for a further hour and neutralized by addition of a few drops of 10% strength HCl. The solvent was evaporated off in vacuo, ether and water were added to the residue, the mixture was extracted several times with ether and the extracts were washed with water and dried over MgSO$_4$. Evaporation of the ether in vacuo gave an oil, which was purified by chromatography on 800 g of silica gel (toluene). 12.74 g (83%) of the title compound were obtained in the form of a colorless oil.

R$_F$: 0.13 (toluene).

IR (CHCl$_3$) 1740–1710 cm$^{-1}$ (C=O, β-ketoester).
$^1$H-NMR (250 MHz, CDCl$_3$) δ 1.49 (s, 9H, C(CH$_3$)$_3$), 3.22 (s. 2H, CH$_2$), 3.52 (s. 2H, CH$_2$), 3.68 (s. 2H, CH$_2$) and 7.33 (s. 5H, Ph).

C$_{15}$H$_{20}$O$_3$S (280.4)
calculated: C 64.3, H 7.2, S 11.4; found: C 64.3, H 7.2, S 11.3.

EXAMPLE 28

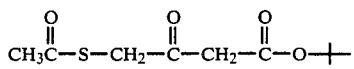

tert.-Butyl 4-acetylthioacetoacetate 2.40 g (21.0 mmols) of dry potassium thioacetate were added to a solution, cooled to 0° C., of 3.85 g (20.0 mmols) of tert.-butyl 4-chloroacetoacetate in 40 ml of anhydrous acetonitrile and the mixture was stirred at this temperature for 30 minutes. Thereafter, the mixture was poured into a mixture of NaCl solution and ethyl acetate, the organic phase was separated off and extracted with 2×30 ml of ethyl acetate and the extracts were washed with water and dried over MgSO$_4$. After the solvent had been evaporated off in vacuo and the residue had been chromatographed on 60 g of silica gel (toluene:ethyl acetate 95:5), 3.87 g (83%) of the title compound were obtained as a colorless oil, R$_F$:0.2 (toluene:ethyl acetate 95:5).

IR (CHCl$_3$) 1740-1710 cm$^{-1}$ (C=O).

$^1$H-NMR (250 MHz, CDCl$_3$) 1.50 (s. 9H, C(CH$_3$)$_3$), 2.42 (s. 3H, CH$_3$CO$_3$), 3.53 (s. 2H, CH$_2$) and 3.90 (s, 2H, CH$_2$).

EXAMPLE 29

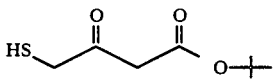

tert.-Butyl 4-mercaptoacetoacetate 45 drops of a 1N solution of sodium methylate in methanol were added to a solution of 465 mg (2 mmols) of tert.-butyl 4-acetylthioacetoacetate in 4 ml of anhydrous methanol and the mixture was stirred at room temperature under nitrogen until the reaction was complete (thin layer chromatography check). Thereafter, the methanol was evaporated off in vacuo and the residue was purified by "flash chromatography" on 40 g of silica gel (toluene:ethyl acetate 94:6), 157 mg (41%) of the title compound were obtained as a colorless oil, R$_F$: 0.13 (toluene:ethyl acetate 94:6).

IR (CHCl$_3$) 3480, 2986, 1712 and 1152 cm$^{-1}$.

NMR (250 MHz, CDCl$_3$) δ 1.5 (s. 9H, C(CH$_3$)$_3$), 2.6-3.8 (m, 5H).

Boiling point about 150° C./0.5 mm, micro-bulb tube.

C$_8$H$_{14}$O$_3$S (190.3) calculated: C 50.50, H 7.42; found: C 50.6, H 7.4

The compound obtained in Example 29 was reacted as described in the reaction sequence of Examples 3, 4, 5, 11, 12, 13 and 14 to give tert.-butyl (6R, 7S)-7-[(2R)-2-tert.-butoxycarbonylamino-2-(4-tert.-butoxycarbonylaminophenyl)acetamido]-3-chloro-8-oxo-5-thia-1-azabicyclo[4.2.0]oct-2-ene-2-carboxylate.

EXAMPLE 30

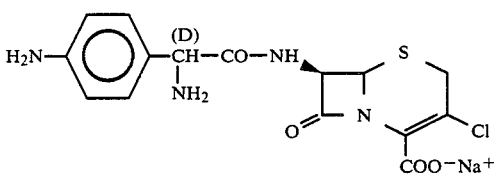

Sodium (6R, 7R)-7-[(2R)-2-amino-2-(4-aminophenyl)-acetamido]-3-chloro-8-oxo-5-thia-1-azabicyclo[4.2.0]oct-2-ene-2-carboxylate As described for Example 10, 768 mg (72%) of the title compound were obtained in a purity of 87% (high pressure liquid chromatography) from 2.08 g (2.78 mmols) of tert.-butyl (6R, 7R)-7-[(2R)-2-tert.-butoxycarbonylamino-2-(4-tert.-butoxycarbonylaminophenyl)acetamido]-3-chloro-8-oxo-5-thia-1-azabicyclo[4.2.0]oct-2-ene-2-carboxylate.

IR (KBr): 3500-2800 (b), 1770 (C=O, β-lactam), 1680 and 1520 (amide) and 1600 cm$^{-1}$ (COONa).

$^1$H-NMR (250 MHz, DCO$_2$D) 3.50, 3.83, (AB, J=19 Hz, 2H, (CH$_2$S), 5.20, (d, J=4.5 Hz, 1H, H-6), 5.60 (s, 1H, CHCO), 5.83 (d, J=4.5 Hz, 1H, H-7), 7.71 and 7.78 (AB, J=7 Hz, 2H, H$_{aromatic}$).

EXAMPLE 31

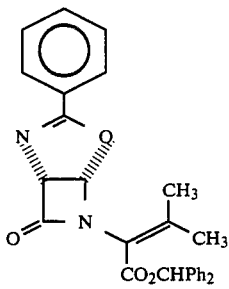

558 μl (4.0 mmols) of triethylamine were added to a solution of 4.53 g (10.0 mmols) of diphenylmethyl 2-[(1R,5S)-3-phenyl-7-oxo-4-oxa-2,6-diazabicyclo[3.2.0-]hept-2-en-6-yl)]-3-methylbut-3-enoate in 250 ml of andhydrous methylene chloride and the mixture was stirred at room temperature for 6 hours. It was then poured into 300 ml of ice-cold 1N HCl and extracted with 2×50 ml of methylene chloride and the extracts were washed with 250 ml of saturated NaHCO$_3$ solution and water and dried over MgSO$_4$. After the solvent had been evaporated off in vacuo and the residue had been chromatographed on 300 g of silica gel (toluene:ethyl acetate 85:15), 3.81 g (84%) of diphenylmethyl 2-[(1R,5S)-3-phenyl-7-oxo-4-oxa-2,6-diazabicyclo[3.2.0-]hept-2-en-6-yl)]-3-methylbut-2-enoate were obtained as a colorless rigid foam, R$_F$ 0.54 (ether).

IR (KBr): 1783 (C=O, β-lactam), 1722 (C=O, ester) and 1632 cm$^{-1}$ (C=N).

$^1$H-NMR (200 MHz, CDCl$_3$): δ=1.83 (s. 3H, CH$_3$), 2.28 (s. 3H, CH$_3$), 5.40 (s, j=4 Hz; 1H H-5), 6.08 (d, J=4 Hz; 1H, H-1), 6.95 (s, 1H, COOCHph$_2$), 7.3–7.6 (m, 13H, C$_6$H$_5$) and 7.95 (m, 2H, o-phenyl-H).

C$_{28}$H$_{24}$N$_2$O$_4$ (452.5) calculated: C 74.32, H 5.32, N 6.19; found: C 74.0, H 5.3, N 6.2.

EXAMPLE 32

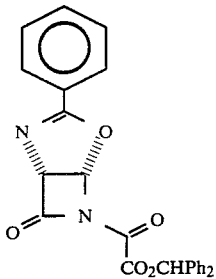

An ozone-oxygen mixture was passed through a solution, cooled to −70° C., of 1.50 g (3.32 mmols) of diphenylmethyl 2-[(1R, 5S)-3-phenyl-7-oxo-4-oxa-2,6-diazabicyclo[3.2.0]hept-2-en-6-yl)]-3-methyl-2-enoate in 50 ml of anhydrous methylene chloride until a blue coloration was obtained. The mixture was then flushed with nitrogen for 10 minutes in order to remove excess ozone, and 1.95 ml (26.52 mmols) of dimethyl sulphide were subsequently added at −70° C. The mixture was stirred at −10° C. for 30 minutes and at room temperature for 1 hour and the solvent was then evaporated off in vacuo. The residue was taken up in 100 ml of methylene chloride and the mixture was washed with saturated NaHCO$_3$ solution and water and dried over MgSO$_4$. The organic phase was concentrated in vacuo, the residue was taken up in a little chloroform, ether was added and the mixture was left to stand. 989 mg (70%) of diphenylmethyl 2-[(1R,5S)-3-phenyl-7-oxo-4-oxa-2,6-diazabicyclo[3.2.0]hept-2-en-6-yl]-2-oxo-acetate were obtained as colorless crystals, melting point 182° C., R$_F$ 0.37 (ethyl acetate:hexane 1:1)—[decomposes on contact with silica gel]—[α]$_D^{20}$ 35.5° (1.006% in chloroform).

IR (KBr): 1817 (C=O, β-lactam), 1754 (C=O, ester), 1712 (C=O, amide) and 1640 cm$^{-1}$ (C=N).

$^1$H-NMR (200 MHz, CDCl$_3$): δ=5.55 (d, J=4.5 Hz; 1H, H-5), 6.54 (d, J=4.5 Hz; 1H, H-1), 7.07 (s, 1H, COOCHph$_2$), 7.2–7.6 (m, 13H, C$_6$H$_5$) and 7.9 (m, 2H, o-phenyl-H). MS (70 eV): m/e=426 (M$^+$); calculated 426.4. C$_{25}$H$_{18}$N$_2$O$_5$ (426.4) calculated C 70.42, H 4.25, N 6.57; found C 70.4, H 4.3, N 6.7.

EXAMPLE 33

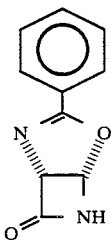

36 ml of a 0.002% strength solution of sodium methanolate in methanol were added to a suspension of 552 mg (1.29 mmols) of diphenylmethyl 2-[(1R, 5S)-3-phenyl-7-oxo-4-oxa-2,6-diazabicyclo[3.2.0]hept-2-en-6-yl)]-2-oxo-acetate in 108 ml of anhydrous methanol and the mixture was stirred at room temperature for 15 minutes. 21 μl of glacial acetic acid were then added and the methanol was evaporated off in vacuo. The residue was dissolved in 100 ml of methylene chloride and the solution was washed with saturated NaHCO$_3$ solution and water and dried over MgSO$_4$. After the solvent had been evaporated off in vacuo and the residue had been chromatographed on 20 g of silica gel (ethyl acetate:hexane 6:4), 112 mg of (1R, 5S)-3-phenyl-7-oxo-4-oxa-2,6-diazabicyclo[3.2.0]hept-2-ene were obtained as colorless crystals, melting point 169° C., R$_F$: 0.23 (ether), [α]$_D^{20}$= −114.8° (0.836% in acetone).

IR (KBr): 1772 (C=O, β-lactam) and 1616 cm$^{-1}$ (C=O, C=N). $^1$H-NMR (200 MHz, DMSO): δ=5.35 (dd, J=4 Hz, J=4 Hz;

1H, H-5), 6.11 (d, J=4 Hz; 1H, H-1), 7.5–7.7 (m, 3H, C$_6$H$_5$), 7.93 (m, 2H, o-C$_6$H$_5$) and 9.36 (d, J=4 Hz; 1H, NH).

EXAMPLE 34

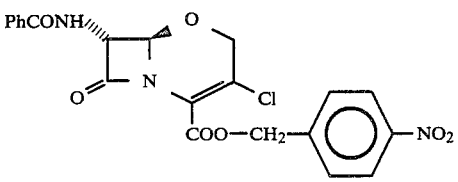

4-Nitrobenzyl(6R,7R)-7-benzoylamino-3-hydroxy-8-oxo-5-oxa-1-azabicyclo[4.3.0]oct-2-ene-2-carboxylate As described for Example 11, 1.22 g (26%) of the title compound were obtained as colourless crystals from 4.39 g (10 mmol) 4-nitrobenzyl (6R,7R)-7-benzoylamino-3-hydroxy-8-oxo-5-oxa-1-azabicyclo[4.2.-0]oct-2-ene-2-carboxylate and 1.40 ml (16 mmol) phosphorus trichloride.

melting point: 192° C., R$_F$: 0.35 (toluene:ethyl acetate 7:3).

IR (KBr): 1791 (C=O, β-lactam), 1733 (C=O, ester), 1642 und 1516 (amide), 1346 cm$^{-1}$ (NO$_2$, sym.).

$^1$H-NMR (250 MHz, CDCl$_3$-DMSO) δ 4.48, 4.54 (AB, j=17 Hz, 2H, CH$_2$O), 4.99 (d, J=7.5 Hz, 1H, H-7), 5.33 (s, 1H, H-6), 5.43, 5.54 (AB, J=13 Hz, 2H, CH$_2$-benzyl), 7.4–7.6 (m, 3H, Ph), 6.75 (d, J=10 Hz, 2H, PNB), 7.96 (m, 2H, o-benzoyl-H), 8.24 (d, J=10 Hz, 2H, PNB, 9.18 (d, J=7.5 Hz, 1H, NH).

C$_{21}$H$_{16}$ClN$_3$O$_7$ (457.8): calculated: C 55.09, H 3.52, N 9.18; found: C 55.4, H 3.7, N 9.0.

EXAMPLE 35

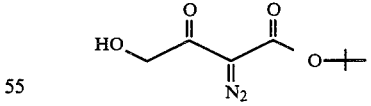

tert.Butyl 2-diazo-4-hydroxy-3-oxo-butanoate

As described for Example 34, 3.43 g (71%) of the title compound were obtained as crystals, mp: 35° C., R$_F$: 0.36 (toluene:ethyl acetate 4:1) from 4.2 g (24.1 mmol) tert.-butyl 4-hydroxyacetoacetate and 5.2 g (26.5 mmol) p-toluenesulphonic acid azide after 3 h at 0° C. followed by 30 min. at room temperature and chromatography of the crude product on 200 g of silica gel (toluene:ethyl acetate 4:1).

IR (CHCl$_3$): 3495 (OH), 2982, 2141 (N$_2$), 1709 (C=O), 1643 (C=O), 1335, 1137, 990 cm$^{-1}$.

¹H-NMR (250 MHz, CDCl₃) δ 1.52 (s, 9H, C(CH₃)₃), 3.48 (t, J=5 Hz, 1H, CH₂OH), 4.59 (d, J=5 Hz, 2H, CH₂OH).

$C_8H_{12}N_2O_4$ (200.2): calculated: C 48.00, H 6.04; found: C 48.0, H 6.1.

EXAMPLE 36

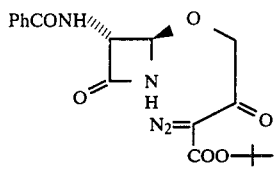

tert.-Butyl 4-[3(R)-benzoylamino-2-azetidinon-4(R)-yloxy]-2-diazo-3-oxo-butanoate (a) 90 μl of boron trifluoride etherate were added to a suspension of 564 mg (3.0 mmol) (1R,5S)-3-phenyl-4-oxa-2,6-diazabicyclo[3.2.0]hept-2-en-7-one and 1.08 g (5.4 mmol-1.8 equiv.) tert.-butyl 2-diazo-4-hydroxy-3-oxo-butanoate in 12 ml of anhydrous tetrahydrofuran at 0° C. The cooling bath was removed and after 10 minutes a clear, light yellow solution formed. After 20 minutes it was poured into a mixture of NaHCO₃ solution, ice and methylene chloride. The mixture was extracted with methylene chloride (3×), washed with water and dried over magnesium sulphate. After the solvent had been evaporated off in vacuo and the residue had been crystalized from methylene chloride-ether-pentane, 861 mg (74%) of the title compound were obtained as light yellow crystals, melting point: 98° C., R_F: 0.29 (toluene:ethyl acetate 2:3). Spectroscopical data identical to Example 4.

(b) As described above, 1.36 g (70%) of the title compound were obtained as crystals, melting point: 103° C. from 941 mg (5.0 mmol) (1R,5S)-3-phenyl-4-oxa-2,6-diazabicyclo[3.2.0]hept-2-en-7-one and 1.10 g (5.5 mmol—1.1 equiv.) tert.-butyl 2-diazo-4-hydroxy-3-oxo-butanoate after a reaction time of 20 minutes.

EXAMPLE 37

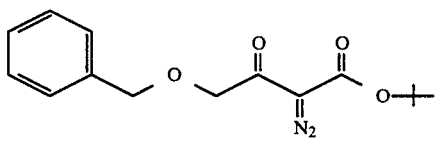

tert.-Butyl 4-benzyloxy-2-diazo-3-oxo-butanoate 5,54 ml (40 mmols—2 equivalents) of triethylamine was added dropwise to a solution, cooled to 0° C., of 5,29 g (20 mmols) of tert.-butyl 4-benzyloxyacetoacetate and 4,34 g. (22 mmols) of 4-toluenesulphonyl azide in 40 ml of anhydrons acetonitrile. The mixture was stirred for 30 minutes at 0° C., treated with 8 g of Celite and evaporated in vacuo. Chromatography of the residue on 100 g of silica gel (toluene:ethyl acetate 95:5) yielded 3,98 g of the title compound as colorless crystals, melting point: 68° C., R_F: 0,31 (toluene:ethyl acetate 95:5).

IR (KBr): 2144 (N₂), 1700, 1673 cm⁻¹.

¹H-NMR (300 MHz, CDCl₃) δ 1,51 (s, 9H, C(CH₃)₃), 4,59 (s, 2H, CH₂) 4,67 (s, 2H, CH₂), 7,3–7,5 (m, 5H, Ph).

$C_{15}H_{18}N_2O_4$ (290,3): calculated: C 62,06, H 6,23, N 9,65; found: C 62,1, H 6,2, N 9,6.

It will be understood that the specification and examples are illustrative but not limitative of the present invention and that other embodiments within the spirit and scope of the invention will suggest themselves to those skilled in the art.

We claim:

1. A process for the preparation of a 7-acylamino-3-hydroxy-2-cephem-4-carboxylic acid, 7-acylamino-3-hydroxy-1-dethia-1-oxa-3-cephem-4-carboxylic acid or derivative thereof of the formula

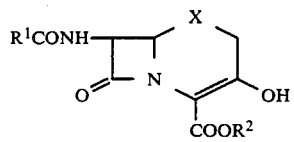

in which

R¹ is hydrogen or optionally substituted alkyl, alkenyl, alkinyl, aralkyl, aryl, heteroaryl, heteroaralkyl, aryloxyalkyl, heteroaryloxyalkyl, alkoxyalkyl, arylthioalkyl, heteroarylthioalkyl, alkylthioalkyl, alkoxy, aryloxy, alkylthio or arylthio, R² is hydrogen, a carboxy-protective group or a pharmaceutically useful ester radical, and X is sulphur or oxygen, which comprises:

(a) reacting a compound of the formula

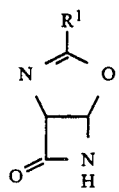

with a compound of the formula

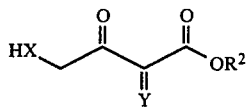

in which R² and X have the abovementioned meaning and Y represents diazo (N₂) or hydrogen (H₂) in an inert solvent in the presence of a Lewis acid or proton acid catalyst, selected from the group consisting of trifluoroacetic acid, trifluoromethanesulphonic acid, perchloric acid, tetrafluoboric acid, hydrochloric acid, quadratic acid, p-toluenesulphonic acid, camphorsulphonic acid, polyphosphoric acid, boron trifluoride, zinc-II chloride, silicon tetrachloride, tin-II chloride, titanium-IV chloride, antimony-V chloride, iron-III chloride, antimony-III chloride, trimethylsilyl trifluoromethanesulphate, trimethylsilyl trifluoroacetate, an acid ion exchanger and silica gel, the compounds thus obtained, for Y being hydrogen (H₂)—(in case of Y=diazo (N₂) directly the compounds of formula (2) are obtained) thereby to produce a compound of the formula

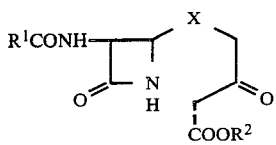

(b) reacting such compound with an azide in a solvent in the presence of a base selected from the group consisting of an alkali metal carbonate, alkali metal amide, triethylamine, diethylamine, diisopropylethylamine, pyridine, dimethylaniline, 1,5-diazabicyclo-undec-5-ene (DBU) and DBN to give a compound of the formula

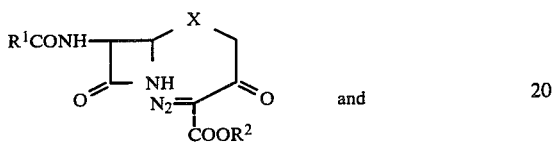

and (c) converting said compound at a temperature of about 40°–120° C. to the desired product by
  (i) irradiation with a light source of wavelength ≧300 nm
  (ii) warming in the presence of catalyst selected from the group consisting of complexes or salts of transition metals or elemental transition metals.

2. A process according to claim 1, wherein step (c) is carried out in benzene, toluene, tetrahydrofuran or methylene chloride.

3. A process according to claim 2, wherein step (c) (i) is carried out in benzene, toluene, CCl$_4$, CCl$_2$, ether, tetrahydrofuran or dioxane.

4. A process according to claim 1, wherein step (b) is effected with an optionally substituted methane-, benzene- or naphthalene-sulphonyl azide.

5. A process according to claim 4, wherein the azide is selected from the group consisting of toluene-sulphonyl azide, 4-dodecylbenzenesulphonyl azide and 4-carboxybenzenesulphonyl azide.

6. A process for the preparation of a 7-acylamino-3-hydroxy-2-cephem-4-carboxylic acid, 7-acylamino-3-hydroxy-1-dethia-1-oxa-3-cephem-4-carboxylic acid or derivative thereof of the formula

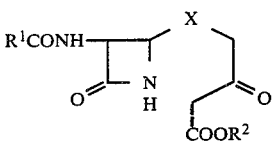

in which
R$^1$ is hydrogen or optionally substituted alkyl, alkenyl, alkinyl, aralkyl, aryl, heteroaryl, heteroaralkyl, aryloxyalkyl, heteroaryloxyalkyl, alkoxyalkyl, arylthioalkyl, heteroarylthioalkyl, alkylthioalkyl, alkoxy, aryloxy, alkylthio or arylthio,
R$^2$ is hydrogen, a carboxy-protective group or a pharmaceutically useful ester radical, and
X is sulphur or oxygen,
which comprises:

(a) reacting a compound of the formula

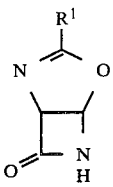

with a compound of the formula

HX—CH$_2$—C≡C—COOR$^2$ in which R$^2$ and X have the above-mentioned meaning to form an intermediate compound having a triple bond, and hydrating the triple bond, thereby to produce a compound of the formula

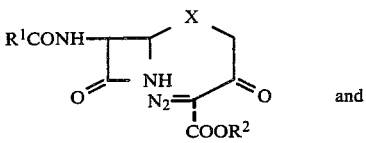

(b) reacting such compound with an azide in a solvent in the presence of a base selected from the group consisting of an alkali metal carbonate, alkali metal amide, triethylamine, diethylamine, diisopropylethylamine, pyridine, dimethylaniline, 1,5-diazabicyclo-undec-5-ene (DBU and DBN to give a compound of the formula

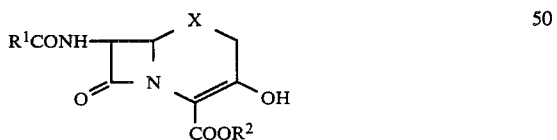

and (c) converting said compound at a temperature of about 40°–120° C. to the desired product by
  (i) irradiation with a light source of wavelength ≧300 nm
  (ii) warming in the presence of a catalyst selected from the group consisting of complexes or salts of transition metals or elemental transition metals.

7. A process according to claim 6, wherein step (c) is carried out in benzene, toluene, tetrahydrofuran or methylene chloride.

* * * * *

UNITED STATES PATENT AND TRADEMARK OFFICE
CERTIFICATE OF CORRECTION

PATENT NO. : 4,616,084
DATED : October 7, 1986
INVENTOR(S) : Dieter Häbich, et al.

It is certified that error appears in the above-identified patent and that said Letters Patent are hereby corrected as shown below:

| | |
|---|---|
| Abstract, line 33 | Correct bottom of formula as follows: 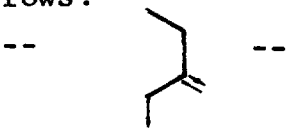 |
| Col. 8, line 5 and Col. 15 line 45 | Correct top left of formula as follows: 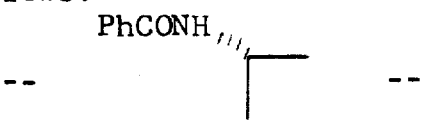 |
| Col. 8, line 55 | Delete "has" and substitute --as-- |
| Col. 10, line 29 | Delete bottom left of formula and substitute 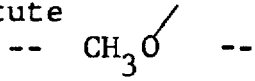 |
| Col. 10, line 68, last formula | Delete last formula and substitute -- $-SC(CH_3)_3$ -- |
| Col. 11, line 5 | Delete first formula and substitute -- $-OC(CH_3)_3$ -- |
| Col. 16, line 50 | Before "7.5" delete "b" |
| Col. 17, line 13 | Correct spelling of --solution-- |
| Col. 17, line 28 | Before "7.85" delete "b" |
| Col. 19, line 5 | Correct spelling of --ethyldiisopropylamine-- |

UNITED STATES PATENT AND TRADEMARK OFFICE
CERTIFICATE OF CORRECTION

PATENT NO. : 4,616,084                    Page 2 of 4
DATED      : October 7, 1986
INVENTOR(S): Dieter Häbich, et al.

It is certified that error appears in the above-identified patent and that said Letters Patent are hereby corrected as shown below:

Col. 20, line 31 and        Delete "cm$^{31}$ $^1$" and substitute
  Col. 21, lines 10, 68       --cm$_{-1}$--
Col. 20, line 34            Delete "1Hz" and substitute
                              --1H--
Col. 20, line 50            After "1" insert -- - --
Col. 20, line 63            Correct top right of formula as
                              follows: 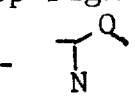

Col. 22, line 31            After "5 g" insert --of--
Col. 22, line 38            Delete "-OCH$_2$-" and substitute
                              -- -OCH$_{\underline{2}}$- --
Col. 22, line 54            Correct spelling of --azetidinon--
Col. 23, line 10 and        Delete "CH$_2$OH" and substitute
  Col. 25, line 45            --CH$_{\underline{2}}$OH--
Col. 23, line 12, Col. 25,  Delete "CH$_2$OH" and substitute
  line 46 and Col. 33, line 2  --CH$_2$OH--
Col. 23, line 54            Delete "N 4.7" and substitute
                              --H 4.7--
Col. 23, line 64            After "35" delete "ml" and sub-
                              stitute --mg--
Col. 25, line 63            Correct spelling of --trifluor-
                              ide--
Col. 27, line 38            Delete "CH2O" and substitute
                              --CH$_2$O--
Col. 27, line 42            Delete "H17" and substitute
                              --H$_{17}$--

UNITED STATES PATENT AND TRADEMARK OFFICE
CERTIFICATE OF CORRECTION

PATENT NO. : 4,616,084
DATED : October 7, 1986
INVENTOR(S) : Dieter Häbich, et al.

Page 3 of 4

It is certified that error appears in the above-identified patent and that said Letters Patent are hereby corrected as shown below:

| | |
|---|---|
| Col. 29, line 21 | Delete "0.2" and substitute --0.24-- |
| Col. 28, line 2, Col. 30, line 62 and Col. 32, line 41 | Delete "j" and substitute --J-- |
| Col. 29, line 21 | Delete "$R_F$" and substitute --$R_f$-- |
| Col. 29, line 35 | Delete "1N" and substitute --1 $\underline{N}$-- |
| Col. 29, line 65 | Bottom right of formula delete " $\searrow_{Cl}$ " and substitute -- $\searrow_{\underline{Cl}}$ -- |
| Col. 30, lines 41, 42 | Correct spelling of --anhydrous-- |
| Col. 30, line 64, Col. 32, line 12 (2 instances), and lines 13 and 14 | Delete "J=4" and substitute --$\underline{J}$=4-- |
| Col. 32, line 28 | Delete "4.3.0" and substitute --4.2.0-- |

UNITED STATES PATENT AND TRADEMARK OFFICE
CERTIFICATE OF CORRECTION

PATENT NO. : 4,616,084      Page 4 of 4

DATED : October 7, 1986

INVENTOR(S) : Dieter Häbich, et al

It is certified that error appears in the above-identified patent and that said Letters Patent is hereby corrected as shown below:

Col. 33, line 65                        After "CH$_2$)" insert --,--
Col. 35, line 14 and Col. 36,    Before "-undec" insert
  line 39                               --[5.4.0]--
Col. 35, line 26 and Col. 36,    Delete "⅞" and substitute
  line 51                               -- ⅟ --

Signed and Sealed this

Twenty-seventh Day of January, 1987

Attest:

DONALD J. QUIGG

Attesting Officer      Commissioner of Patents and Trademarks